(12) United States Patent
Schultz

(10) Patent No.: US 7,131,559 B2
(45) Date of Patent: *Nov. 7, 2006

(54) ACCURATE DOSING PUMP

(75) Inventor: Robert S. Schultz, Old Greenwich, CT (US)

(73) Assignee: Ben Z. Cohen, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/249,679

(22) Filed: Oct. 13, 2005

(65) Prior Publication Data

US 2006/0027607 A1    Feb. 9, 2006

Related U.S. Application Data

(63) Continuation of application No. 10/476,505, filed as application No. PCT/US02/16539 on May 23, 2002, now Pat. No. 6,991,137.

(60) Provisional application No. 60/329,963, filed on Oct. 17, 2001, provisional application No. 60/302,847, filed on Jul. 3, 2001, provisional application No. 60/292,949, filed on May 23, 2001.

(51) Int. Cl.
*B67D 5/40* (2006.01)

(52) U.S. Cl. ............... 222/377; 222/380; 222/385

(58) Field of Classification Search .......... 222/321.1, 222/321.2, 321.7, 321.9, 377, 380, 383.1, 222/385

See application file for complete search history.

(56) References Cited

U.S. PATENT DOCUMENTS

| | | |
|---|---|---|
| 2,781,953 A | 2/1957 | Sylvander |
| 4,995,867 A | 2/1991 | Zollinger |
| 5,152,435 A | 10/1992 | Stand et al. |
| 5,190,191 A | 3/1993 | Reyman |
| 5,340,289 A | 8/1994 | Konleczynski et al. |
| 5,556,268 A | 9/1996 | Topper et al. |
| 5,816,455 A | 10/1998 | Alpers |
| 5,881,956 A | 3/1999 | Cohen et al. |
| 5,957,338 A | 9/1999 | Lehmann |
| 6,010,036 A | 1/2000 | Bougamont et al. |
| 6,070,137 A * | 5/2000 | Bloebaum et al. .......... 704/227 |
| 6,158,621 A | 12/2000 | Keller |
| 6,196,424 B1 | 3/2001 | Bougamont et al. |
| 6,467,579 B1 | 10/2002 | Simon |
| 6,991,137 B1 * | 1/2006 | Schultz .................. 222/377 |
| 2004/0129734 A1 | 7/2004 | Cohen et al. |
| 2005/0023300 A1 | 2/2005 | Schultz |

* cited by examiner

Primary Examiner—Edward K. Look
Assistant Examiner—John K. Fristoe, Jr.
(74) Attorney, Agent, or Firm—Hoffmann & Baron, LLP

(57) ABSTRACT

With the subject invention, a pump is formed that generally includes a reservoir formed to accommodate at least one fluid dose, and a fluid-collecting chamber in fluid communication with the reservoir. The fluid-collecting chamber includes a dose-control portion which encompasses a volume defined by two dimensions. A first piston is disposed to urge fluid from the reservoir and at least into the dose-control portion. A second piston is disposed to reversibly slide within at least the dose-control portion of the fluid-collecting chamber. A nozzle is also provided which is located such that fluid displaced by the second piston from the dose-control portion is generally urged towards the nozzle. A check valve may be placed in the fluid path between the dose-control portion and the nozzle.

11 Claims, 19 Drawing Sheets

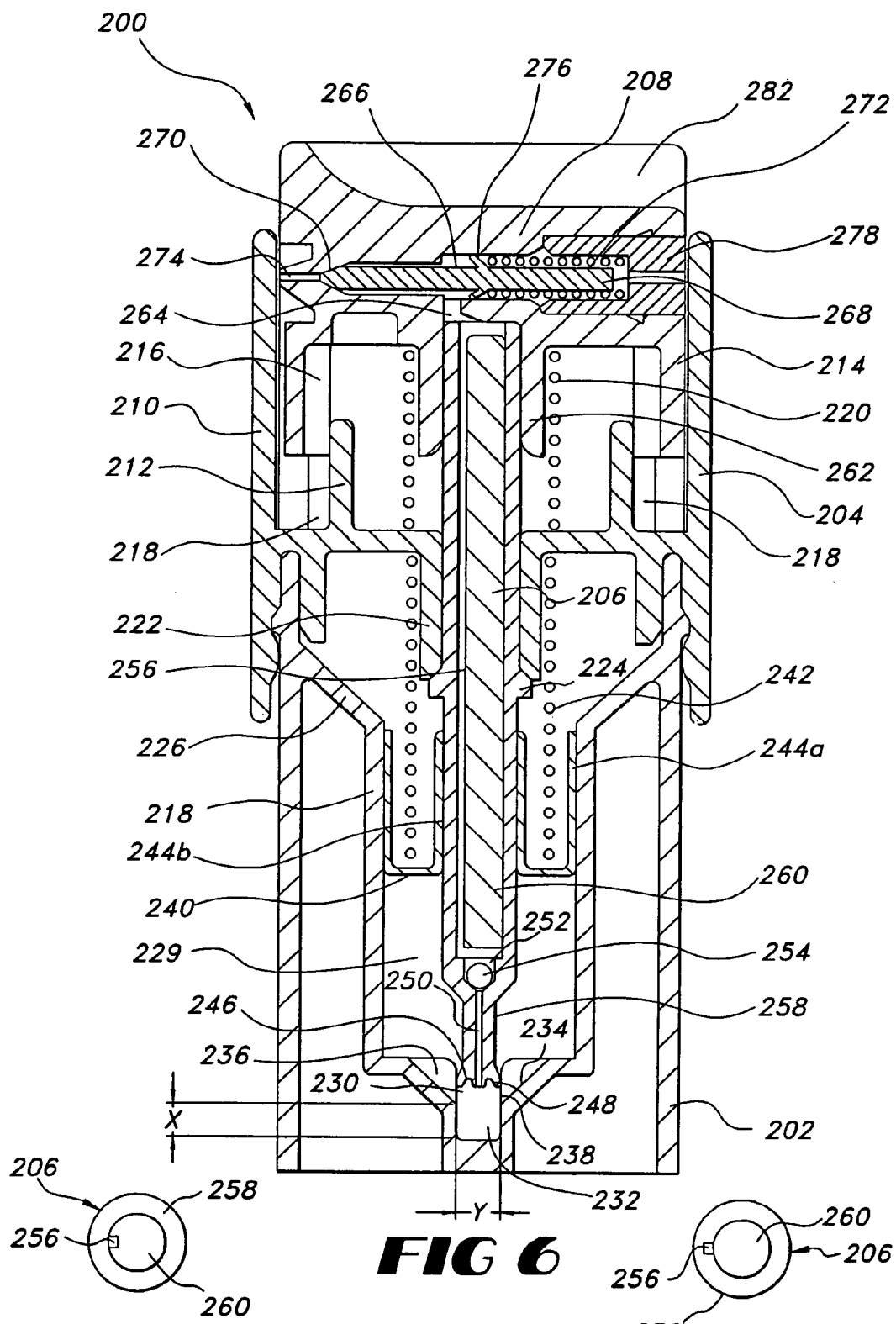

ACCURATE DOSING PUMP

CROSS-REFERENCE TO RELATED APPLICATIONS

This application is a continuation of U.S. application Ser. No. 10/476,505, filed Oct. 30, 2003, now allowed, which was a National Stage Application under §371 of International Application No. PCT/US02/16539, filed May 23, 2002, which claimed priority of U.S. Provisional Application No. 60/292,949, filed May 23, 2001, U.S. Provisional Application No. 60/302,847, filed Jul. 3, 2001, and U.S. Provisional Application No. 60/329,963, filed Oct. 17, 2001.

BACKGROUND OF THE INVENTION

This invention relates to pumps, and, more particularly, to pumps having accurately-controlled dosing.

In the prior art, pumps are used for various applications ranging from administration of health and beauty products (e.g., hand lotion) to lubricants. With the majority of pump applications, high accurate control of a dose is not critical and prior art pumps commonly have dose tolerances in the range of 3 to 5 microliters. Certain applications, however, have been developed which do require highly accurate dose control. For example, pumps have been developed which deliver microdoses of ophthalmic fluid medication (5 microliters to 50 microliters), such as those disclosed in: U.S. Pat. No. 5,152,435, issued Oct. 6, 1992; U.S. Pat. No. 5,881,956, issued Mar. 16, 1999; and, PCT Application No. PCT/US00/23206, filed Aug. 23, 2000. These references are incorporated by reference herein in their respective entireties. As can be appreciated with all drug dispensing technology, accurately controlled dosing is absolutely necessary, particularly with small doses.

SUMMARY OF THE INVENTION

With the subject invention, various embodiments of a pump are provided having highly accurate control of a dose. The pump can be used in various applications, although accurate control is particularly advantageous with microdosing.

With the subject invention, a pump is formed that generally includes a reservoir formed to accommodate at least one fluid dose, and a fluid-collecting chamber in fluid communication with the reservoir. The fluid-collecting chamber includes a dose-control portion which encompasses a volume defined by two dimensions. A first piston is disposed to urge fluid from the reservoir and at least into the dose-control portion. A second piston is disposed to reversibly slide within at least the dose-control portion of the fluid-collecting chamber. A nozzle is also provided which is located such that fluid displaced by the second piston from the dose-control portion is generally urged towards the nozzle. A check valve may be placed in the fluid path between the dose-control portion and the nozzle.

Advantageously, with the pump of the subject invention, a simple design can be provided which has a limited number of critical dimensions controlling the dose amount. Generally, the volume of the dose-control portion of the fluid-collecting chamber controls the pump's dose. In a preferred embodiment, the dose-control portion is cylindrically shaped having two dimensions: a diameter and a height. As such, manufacturing variations affecting the dose amount may be minimized with only two dimensions being implicated (and their respective tolerances) in controlling dosing.

The pumps of the subject invention can be used in various applications, but are particularly well-suited for use with administration of ophthalmic fluid medication.

In another aspect of the subject invention, an adapter is provided which may be used as an alignment aid in operating a pump.

These and other features of the invention will be better understood through a study of the following detailed description and accompanying drawings.

BRIEF DESCRIPTION OF THE DRAWINGS

In the drawing figures, which are merely illustrative, and wherein like reference numerals depict like elements throughout the several views:

FIG. 6 is a schematic of the interior of the pump of the second embodiment;

FIGS. 7a and 7b are cross-sectional views of the piston of the second embodiment;

DETAILED DESCRIPTION OF THE INVENTION

Figure 1:
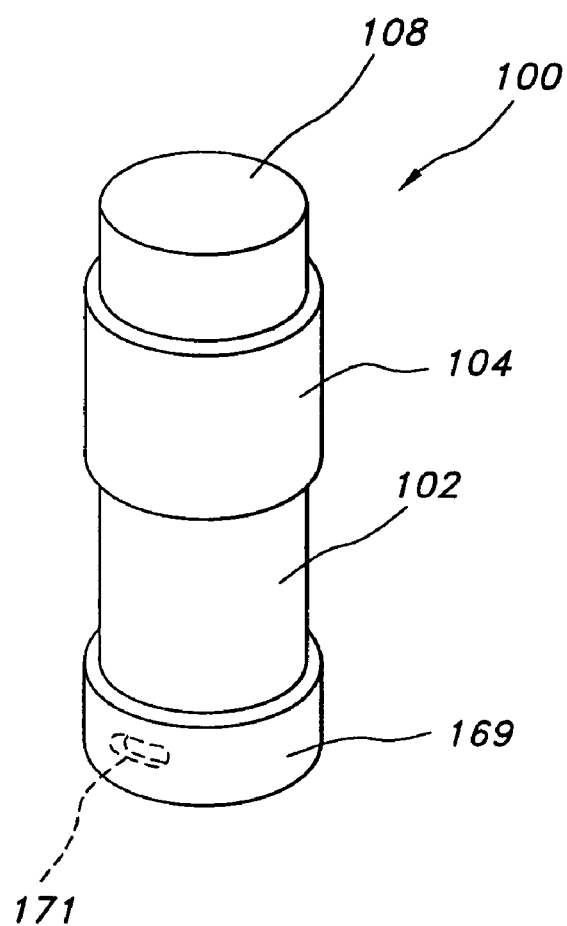
FIG. 1 is a perspective view of a first embodiment of a pump formed in accordance with the subject invention.

Various embodiments of a highly-accurate dose-control pump are described and depicted herein. As will be recognized by those skilled in the art, certain views in the drawings (e.g., FIGS. 2, 6 and 12) are combination cross-sectional and cut-away views which illustrate the internal parts of the various embodiments. It is to be understood that aspects discussed specifically with certain embodiments may be applied to other embodiments. To simplify disclosure herein, not all descriptions are repeated. It is also to be understood that any variation of the disclosed elements of the several embodiments may be utilized which are consistent with the teachings herein.

Figure 3:
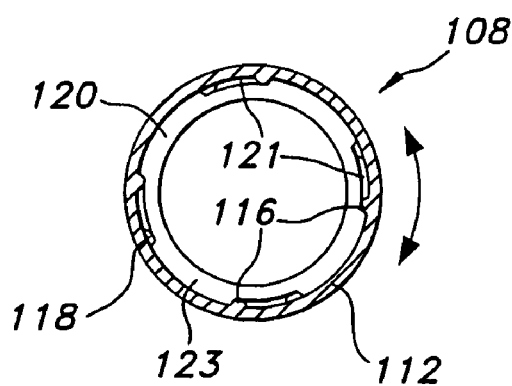
FIG. 3 is a schematic depicting a locking mechanism usable with the subject invention.
Figure 4:
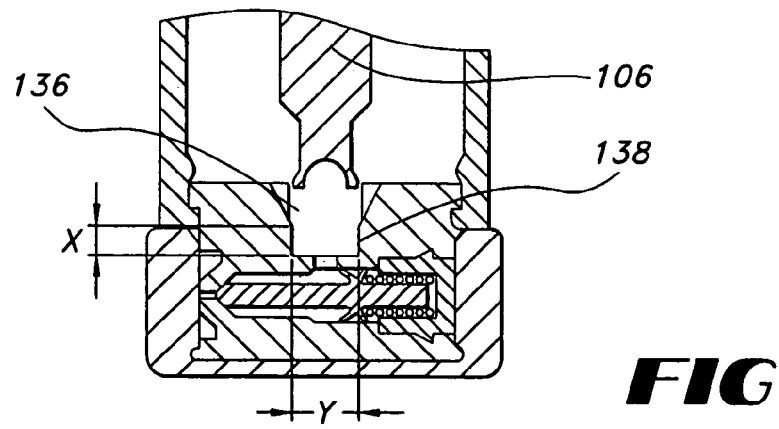
FIG. 4 shows an alternatively dimensioned dose-control portion from that of FIG. 2.

Referring to FIGS. 1–4, a first embodiment of a pump 100 is depicted formed in accordance with principles of the subject invention. The pump 100 is shown to have a cylindrical body, but may be formed in other shapes. The pump 100 includes a housing 102, an end cover 104, and a cap 108 which is used to actuate the pump 100. Upon actuation, a dose of fluid is dispensed from the pump 100. Due to the inventive design herein, the volume of the dispensed doses can be accurately and repeatedly controlled. The pump 100 will be primarily described with reference to FIG. 2. Some exemplary variations are shown in FIGS. 2a and 4 and reference thereto is made appropriately.

Figure 2:
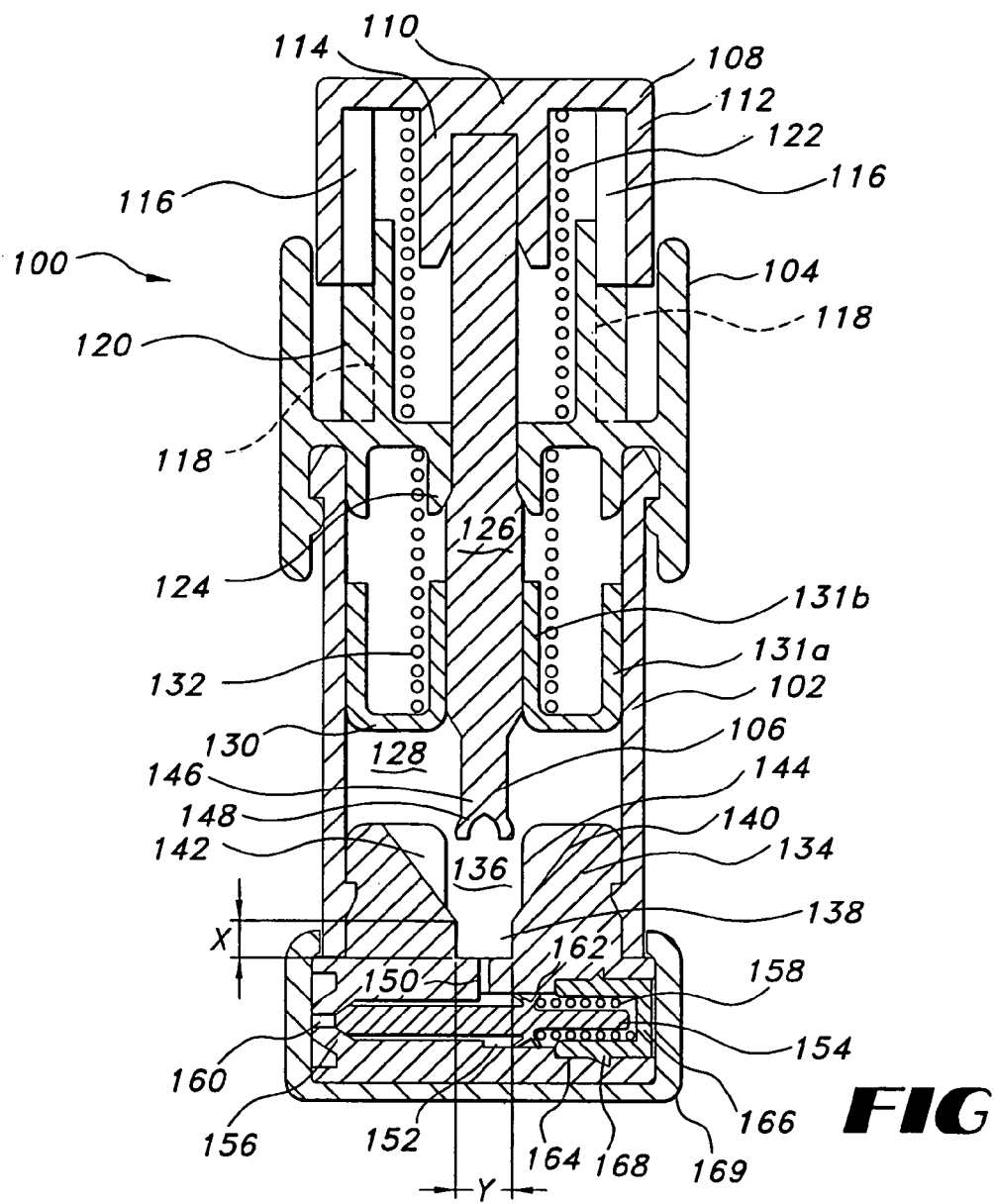
FIG. 2 is a schematic of the interior of the pump of the first embodiment.
Figure 2A:
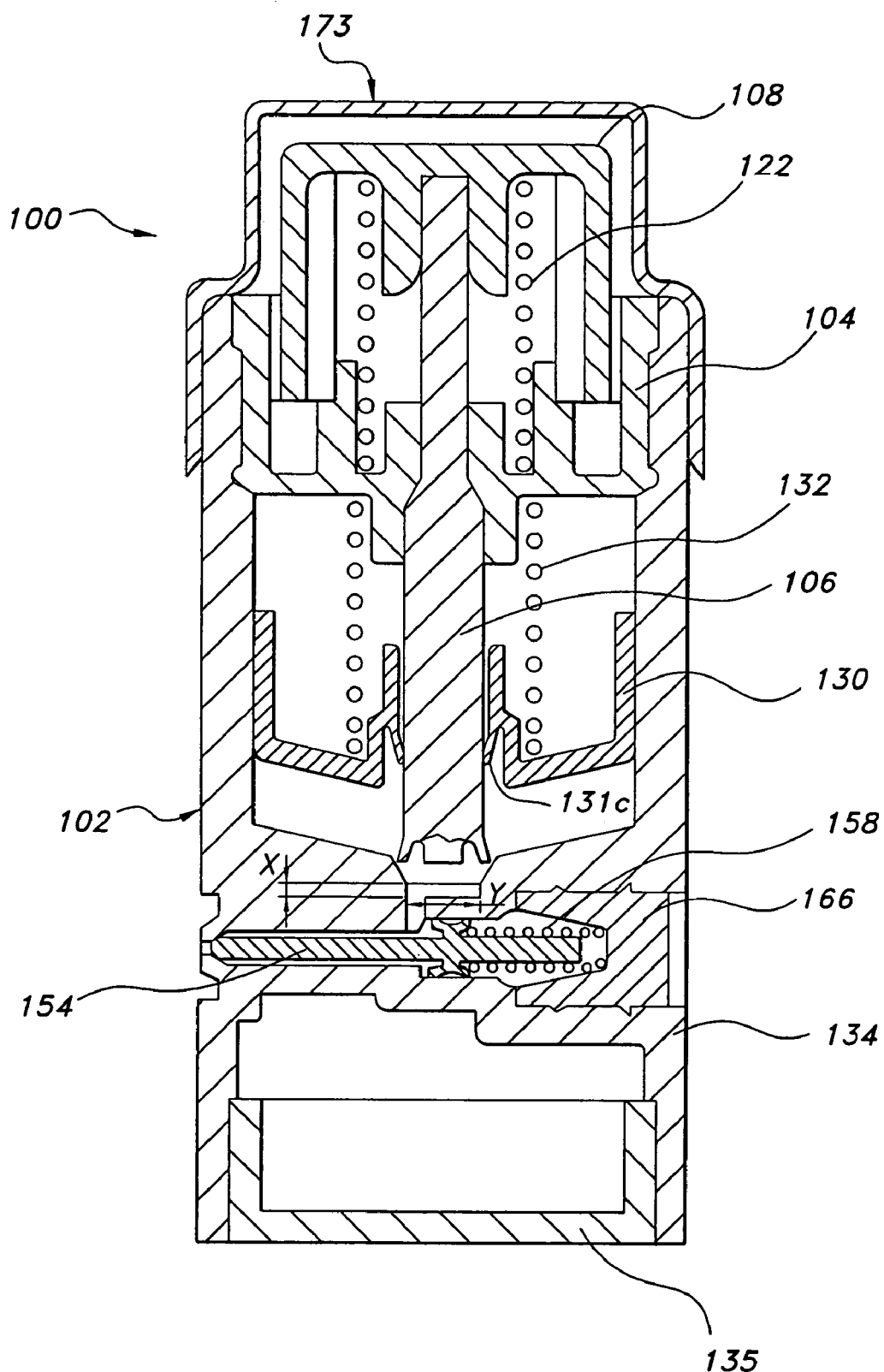
FIG. 2a is a schematic similar to FIG. 2 but with variations of various elements.

With reference to FIG. 2, the housing 102 is mounted, for example by snap-fit or threaded connection, to the end cover 104. A piston 106 is slidably disposed to extend through the end cover 104, and the cap 108 is rigidly mounted to an end of the piston 106. The cap 108 includes a top portion 110 from which depend a side wall 112 and an interior wall 114. The piston 106 is nested within, and fixed to, the interior wall 114 such that a stable connection is formed between the cap 108 and the piston 106. Ribs 116 extend inwardly from the side wall 112 which are circumferentially spaced-apart about the side wall 112. At least one of the ribs 116 should be provided, although, preferably, a plurality is provided. The ribs 116 are formed to slide within slots 118 defined in guidewall 120 of the end cover 104 in providing guidance for downward movement of the cap 108.

The ribs 116 may also be used as a locking mechanism for preventing actuation of the pump 100. Referring to FIG. 3, the guidewall 120 may be formed with cut-outs 121 that correspond to each of the ribs 116 that allow rotation of the cap 108 in its rest state (as shown in FIG. 1). Stop blocks 123 are interposed between the cut-outs 121 to prevent excessive rotation of the cap 108 relative to the guidewall 120. The ribs 116 may be rotated out of registration with the slots 118, thereby preventing downward movement of the cap 108. As described more fully below, downward movement of the cap 108 effectuates actuation of the pump 100. To allow for actuation, the cap 108 is rotated so that the ribs 116 are in registration with the slots 118. Although not shown, as an alternative, the ribs 116 may be formed on the guidewall 120 and the slots 118 on the cap 108, or a combination of ribs 116 and slots 118 may be formed on each component.

A cap spring 122, such as a coil spring, is disposed between the end cover 104 and the cap 108 so as to urge the cap 108 upwardly and away from the end cover 104 in a rest state. Preferably, the inner dimension of the guidewall 120 is selected so as to provide columnar support for the cap spring 122. Shoulders 124 (which may be discontinuous or a continuous annular shoulder) are defined on the end cover 104 which cooperate with an enlarged section 126 of the piston 106 to limit the upper extent of movement of the cap 108/piston 106 composite resulting from upward urging by the cap spring 122. The shoulders 124 and the enlarged section 126 also coact to define a seal with the enlarged section 126 bearing against the shoulders 124.

A reservoir 128 is partially defined by the housing 102 to accommodate fluids, such as ophthalmic fluid medication. A pressure piston 130 defines the upper extent of the reservoir 128, with the pressure piston 130 being biased against any fluid within the reservoir 128 by push spring 132. The reservoir 128 is preferably not vented to atmosphere. Accordingly, the volume of the reservoir 128 must be responsive to reductions of fluid volume located therein to prevent the formation of vacuum and/or disruption of prime. With fluid being dispensed from the pump 100, the volume of the reservoir 128 is reduced by responsive movement of the pressure piston 130. Preferably, the shoulders 124 are dimensioned to provide support for the push spring 132. To inhibit leakage of fluid from the reservoir 128 and about the pressure piston 130, extended annular flanges 131a, 131b are disposed to bear against the housing 102 and the piston 106, respectively, so as to define tortuous leakage paths to stop fluid leakage. Other seals may be provided, such as elastomeric rings and/or biased deflectable seal members 131c (FIG. 2a).

An end block 134 is also mounted to the housing 102 using any technique known to those skilled in the art, such as a snap-fit as shown in FIG. 2. Alternatively, the end block 134 may be unitarily formed with the housing 102 as a single piece, as shown in FIG. 2a. A bottom plug 135 may also be provided to define a flat resting surface for the pump 100, as well as, to close off the interior of the end block 134. With reference again to FIG. 2, the end block 134 defines a portion of the reservoir 128 and is formed with a fluid-collecting chamber 136 that is in open fluid communication with the reservoir 128. A dose-control portion 138 is defined at the lowermost portion of the fluid-collecting chamber 136. With the subject invention, it is intended that fluid accommodated in the reservoir 128 be urged into the fluid-collecting chamber 136 and, in particular, to the dose-control portion 138 by the pressure piston 130. To assist the pressure feed, the end block 134 has tapered portions 140 which converge towards the dose-control portion 138. To guide sliding movement of the piston 106, as will be described in more detail below, fins 142 may extend upwardly from the tapered portions 140 having guide edges 144 shaped and configured to limit off-center movement of the piston 106.

In a preferred embodiment, the dose-control portion 138 encompasses a cylindrical volume having a diameter Y and a height X. The piston 106 is formed with a ram portion 146 having a resilient, inwardly deflectable annular seal 148 (which may be continuous or defined by a plurality of spaced-apart individual seal members) formed thereabout shaped to engage the wall of the dose-control portion 138 in sealing engagement upon the piston 106 sliding thereinto. If a plurality of spaced-apart members are used to define the annular seal 148, it is preferred that the seal members form a continuous annular seal upon being contracted into the dose control portion 138. Because of the dimensioning of the dose-control portion 138 and that the pumping action of the pump 100 occurs only during sliding movement of the piston 106 within the dose-control portion 138, the volume of the doses administered by the pump 100 are substantially controlled by the two dimensions X, Y. The volume of the dose of the pump 100 is generally equal to the volume of the dose-control portion 138. The flexibility of the annular seal 148 of the piston 106 allows for responsiveness to the dimensions X, Y in urging a fluid dose towards a nozzle of the pump 100, as described below.

A channel 150 extends from the dose-control portion 138 into fluid communication with a nozzle control chamber 152 defined within the end block 134. A check valve is preferably disposed in the nozzle control chamber 152 to regulate dose administration. By way of non-limiting example, a nozzle piston 154 may be disposed within the nozzle control chamber 152 which is urged into contact with tapered wall 156 by nozzle spring 158. As such, the nozzle 160 is sealed from the nozzle control chamber 152 in a normal state and prevents fluid from leaking out of the pump 100 due to pressure generated by the pressure piston 130 acting on the entrapped fluid. The nozzle piston 154 is provided with an annular nozzle seal 162 in sealing contact with a wall of the nozzle control chamber 152. To aid in manufacturing the pump 100, the nozzle control chamber 152 may be formed with an open end 164 through which the nozzle piston 154 and the nozzle spring 158 may be inserted. An end plug 166 may be fixed in the open end 164 using any technique known to those skilled in the art, including using an annular detent 168 as shown.

To limit the ingress of contaminants into the nozzle 160, a nozzle cap 169 may be provided which may be removably mounted onto the end block 134. In addition, or alternatively, the nozzle cap 169 may be rotatable about the end block 134 with a cut-out or aperture 171 (shown in dashed lines in FIG. 1) being formed in the nozzle cap 169, so that the nozzle 160 may be selectively exposed and covered as needed. Furthermore, an end cap 173 may be provided which is removably mountable to the housing 102 to selectively cover the cap 108 (FIG. 2a).

In use, the pump 100 is actuated by depressing the cap 108, causing the piston 106 to translate downwardly with the annular seal 148 eventually entering the dose-control portion 138. Tapered portions 140 may facilitate contraction of the annular seal 148 upon downward descent of the piston 106. The annular seal 148 causes the dose-control portion 138 to be sealed from the reservoir 128. Upon further downward translation, the fluid trapped within the dose-control portion 138, the channel 150, and the nozzle control chamber 152 becomes pressurized. Upon sufficient pressure build-up to overcome the spring force of the nozzle spring 158, the pressurized fluid acts against the annular nozzle seal 162 causing the nozzle piston 154 to move away from the tapered wall 156, allowing the nozzle 160 to communicate with the nozzle control chamber 152. As a result, pressurized fluid rushes through the nozzle 160 and is delivered as a dose of fluid. With discharge, pressure decays in the nozzle control chamber 152, and the nozzle piston 154 is urged to its normal state bearing against the tapered wall 156 by the nozzle spring 158. Upon releasing the cap 108, the cap spring 122 causes the cap 108 to return its up, rest position with the piston 106 being withdrawn from the dose-control portion 138. With the piston 106 being removed from the dose-control portion 138, fluid from the reservoir 128 is urged into the fluid-collecting chamber 136, and, in particular, to the dose-control portion 138, to replace the dosed fluid under pressure from the pressure piston 130. Any reduction of volume of fluid in the reservoir 128 is responded to by the push spring 132 and the pressure piston 130.

The dose-control portion 138 may have various configurations depending on the dose requirements. As discussed above, the volume of the dose is generally equal to the volume of the dose-control portion 138. Thus, the dimensions X and/or Y may be varied to vary the dose. In addition, the dimensions X and/or Y may be selected such that bottoming of the piston 106 within the dose-control portion 138 coincides with generation of sufficient pressure to overcome the nozzle spring 158—thus, the bottoming of the piston 106 coincides with an open state of the pump 100, allowing dispensing. As shown in FIG. 4, the fluid-collecting chamber 136 and the dose-control portion 138 are dimensioned for a relatively smaller fluid dose than shown in FIG. 2.

With reference to FIGS. 5–8, a second embodiment of a pump 200 is depicted therein formed in accordance with the principles of the subject invention. In contrast to the first embodiment 100, the pump 200 dispenses fluid from an upper location with the pump 200 in a vertically upright position.

Figure 5:
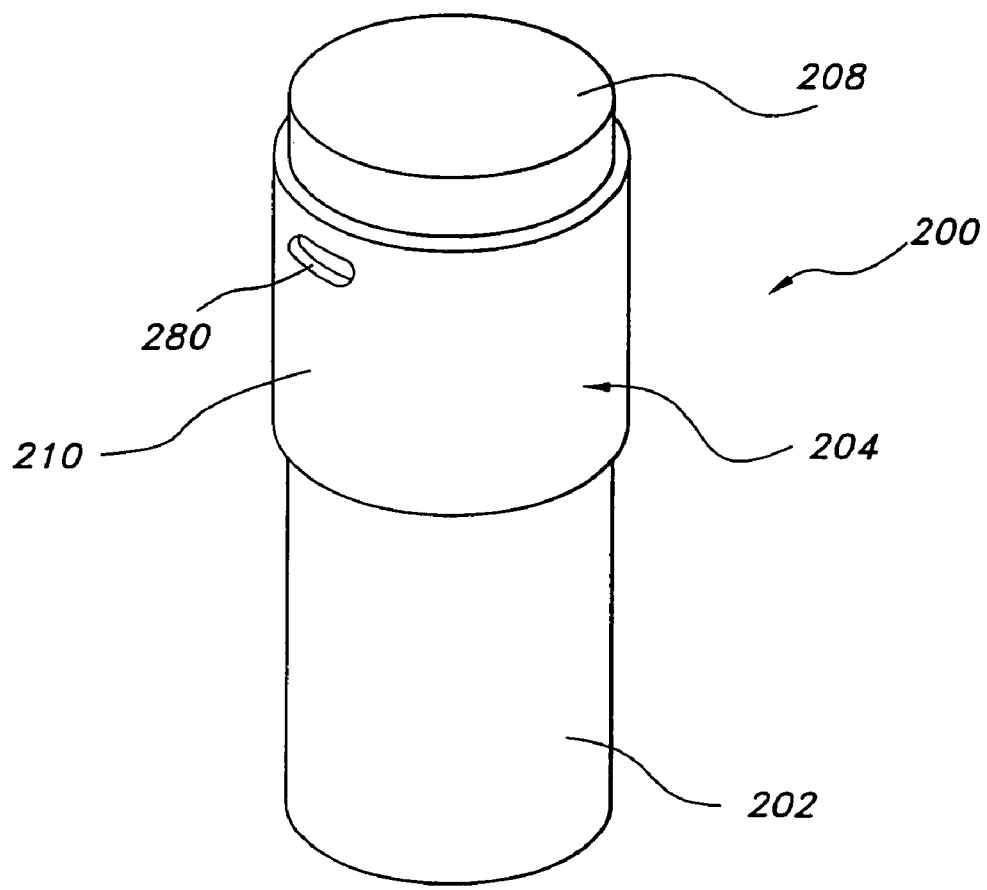
FIG. 5 is a perspective view of a second embodiment of a pump formed in accordance with the subject invention.

Referring to FIGS. 5 and 6, the pump 200 includes a housing 202 which is fixed to an end cover 204 using any technique known to those skilled in the art, such as a snap-fit or threaded connection. A piston 206 extends through the end cover 204, and a cap 208 is mounted to an end of the piston 206.

The end cover 204 includes a tubular shroud 210 which encircles the periphery thereof. An interior wall 212 extends upwardly from the end cover 204, and a skirt 214 depends downwardly from the cap 208 having inwardly protruding ribs 216 circumferentially spaced thereabout. The ribs 216 are formed to slide within slots 218 defined in the interior wall 212. In a preferred arrangement, in a similar manner to that described above, the ribs 216 may act as a locking mechanism in being selectively rotated in and out of registration with the slots 218.

A cap spring 220 is disposed between the end cover 204 and the cap 208 to urge the cap 208 upwardly and away from the end cover 204. Shoulders 222 (which may be discontinuous or continuous and annular) extend downwardly from the end cover 204 to cooperate with an enlarged portion 224 of the piston 206 in preventing upward movement of the piston 206 due to the urging by the cap spring 220. Because of the rigid fixing of the piston 206 to the cap 208, the two components move in concert.

A webbing 226 extends inwardly of the housing 202 and is connected to a cylindrical reservoir wall 228 encircling a reservoir 229 for accommodating fluid, such as ophthalmic fluid medication. The reservoir 229 may be of any diameter within the housing 202; or, alternatively, the housing 202 may define the reservoir 229 (i.e., no webbing 226 is provided). The reservoir wall 228 terminates at one end in a fluid-collecting chamber 230. The lowest portion of the fluid-collecting chamber 230 is a dose-control portion 232 which is preferably cylindrical having a diameter Y and a height X. As with the dose-control portion 138 discussed above, the dose-control portion 232 may be of varying dimensions. The fluid-collecting chamber 230, and in particular the dose-control portion 232, is in open fluid communication with the reservoir 228 to allow fluid from the reservoir 228 to be pressure fed thereinto by pressure piston 240. To facilitate the pressure feed, the fluid-collecting chamber 230 has tapered portions 234. Fins 236 may extend from the tapered portion 234 having inner edges 238 to limit off-center movement of the piston 206.

As with the first embodiment of the invention, the reservoir 229 is not vented but is provided with the pressure piston 240 that defines the upper extent of the reservoir 229 and is biased against fluid in the reservoir by a push spring 242. Preferably, the push spring 242 is disposed about the shoulders 222 to be provided with additional support. Additionally, to prevent leakage about the pressure piston 240, extended annular flanges 244a, 244b are disposed to bear against the reservoir wall 228 and the piston 206, respectively, and to provide tortuous leakage paths to limit fluid leakage. Other seals may be provided, such as elastomeric o-rings, and/or biased, deflectable seal members.

The piston 206 includes a ram portion 246 having formed thereabout an annular seal 248 that is inwardly deflectable. The seal is formed to deflect and bear against the wall of the dose-control portion 238 to generate a seal. A passageway 250 extends from the ram portion 246 and communicates with an inner check-valve chamber 252 defined within the piston 206. A check-valve element 254, such as a check-valve ball as shown in FIG. 6, is disposed within the inner check-valve chamber 252. With the pump 200 in an unactuated state, the check-valve element 254 seals the passageway 250 from the inner check-valve chamber 252. A bore 256 extends from the inner check-valve chamber 252 to an upper end of the piston 206. To ease manufacturing, as shown in FIGS. 7a and 7b, the piston 206 may be formed with an outer sleeve 258 that extends the full length of the piston 206, including the ram portion 246 and the annual seal 248, and a core 260 disposed rigidly therein. In preparing the piston 206, the outer sleeve 258 is first prepared and the check-valve element 254 disposed therein to seat in the inner check-valve chamber 252. Thereafter, the core 260 is inserted and affixed to the outer sleeve using any technique known to those skilled in the art. The bore 256 may be defined by a slot defined in the core 260 and/or a slot defined in the outer sleeve 258. Additionally, the core 260 advantageously reduces the volume of the bore 256. As a result, a minimal number of strokes will be required to prime the pump 200 to allow for an initial use.

The cap 208 includes a mounting wall 262 which is secured about the piston 206. Preferably, the mounting wall 262 is defined to provide support for the cap spring 220. A passage 264 communicates the bore 256 with a nozzle control chamber 266. A nozzle piston 268 is urged against a tapered wall 270 by a nozzle spring 272 to seal nozzle 274. An annular nozzle seal 276 bears against the wall of the nozzle control chamber 266 to form a seal therewith. As with the first embodiment, an end plug 278 may be used to assemble and prepare the internal components of the nozzle control chamber 266. Preferably, a vent 279 is defined in the end plug 278 to allow the nozzle piston 268 to push against the nozzle spring 272 without compressing air located around the nozzle piston 268 rearwardly of the nozzle seal 276. The vent 279 can be sized to control the resistance (and thus the speed) by which the nozzle piston 268 opens and closes. The vent can be utilized with the end plug of the first embodiment, although not shown.

Figure 8:
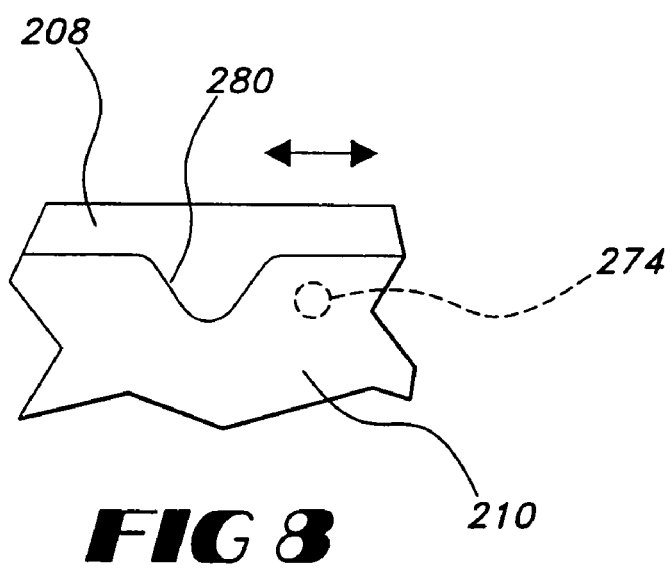
FIG. 8 is an alternative structure of the shroud of the second embodiment having a cut-out defined therein.

With reference to FIGS. 5 and 8, because of the shroud 210, a cut-out or aperture 280 must be formed therein to allow for exposure of the nozzle 274 during discharge. To limit ingress of contaminants into the nozzle 274, the cap 208 may be rotated so that the nozzle 274 is spaced from the cut-out or aperture 280 and shielded by the shroud 210.

To actuate the pump 200, the cap 208 is depressed, causing downward translation of the piston 206. To make use of the pump 200 more comfortable, a finger relief 282 may be defined in the cap 208. Upon sufficient downward translation, the annular seal 248 of the piston 206 engages the dose-control portion 232 and causes the dose-control portion 232 to be sealed from the reservoir 228. With further downward translation, fluid trapped within the dose-control portion 232 becomes pressurized, until sufficient pressure is developed to lift the check-valve element 254 away from the passageway 250 causing open communication between the dose-control portion 232 and the nozzle control chamber 266 via the bore 256. As fluid is driven up the bore 256, pressure within the nozzle control chamber 266 increases until sufficient pressure acts against the annular nozzle seal 276 causing it to separate from the tapered wall 270. With such operation, a dose of fluid is discharged from the nozzle 274. Pressure then decays within the nozzle control chamber 266 and the nozzle piston 268 returns to bear against the tapered wall 270. Also, the check-valve element 254 returns to its rest position sealed against the passageway 250. Upon releasing the cap 208, the cap spring 220 urges the cap 208 upwardly to its rest position along with the piston 206. With the piston 206 separated from the dose-control portion 232, fluid from the reservoir is urged into the dose-control portion 232 by the pressure piston 240. Any reduction in fluid volume within the reservoir 228 is compensated for by the pressure piston 240.

As with all pumps, initial priming is a design consideration which must be taken into account. Before proper dosing of a pump, fluid must be generally drawn through all of a working fluid passageway of a pump. In one manner of priming, initial prime may be obtained by repetitively actuating the pump until several doses have been administered, to ensure proper operation. Alternatively, with reference to FIGS. 9a–c, 10a–c, and 11, initial prime may be obtained by causing a much larger dose to be dispensed than the intended dose, thereby ensuring all surfaces are wetted through less strokes (ideally one stroke).

Figure 9A:
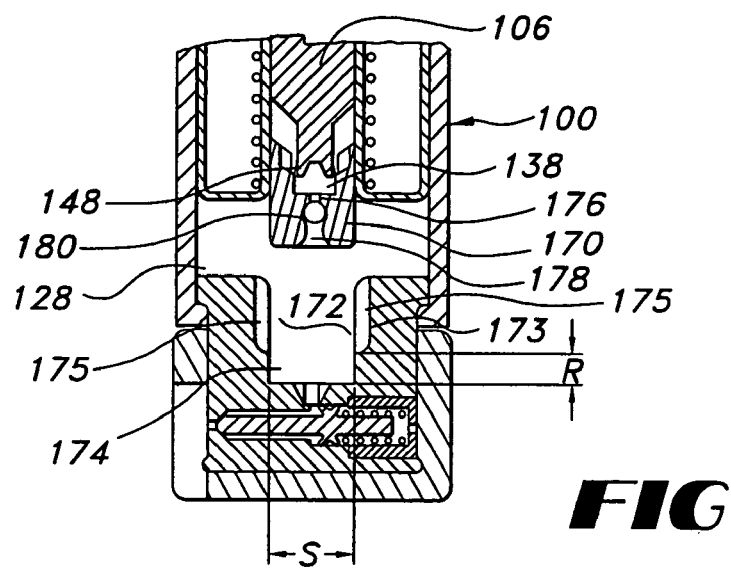
FIGS. 9a–9c are views showing placement of an initial prime block in causing initial prime for the first embodiment of the pump.
Figure 9B:
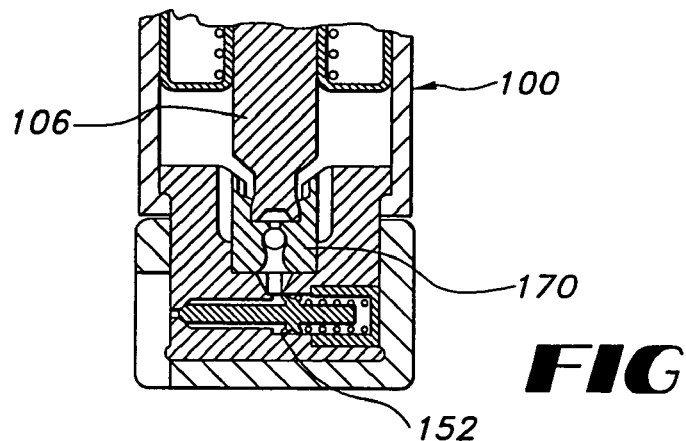
Figure 9C:
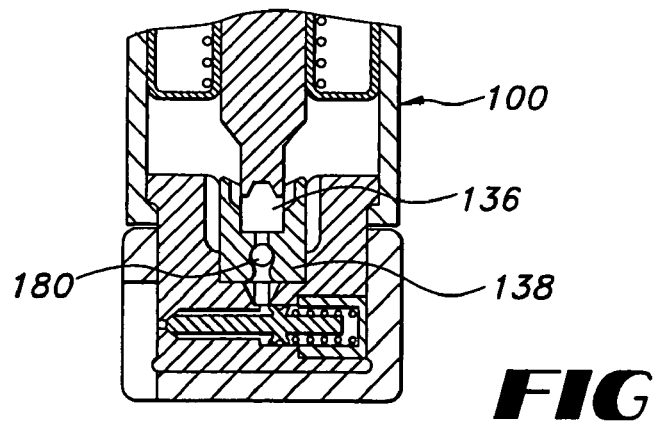

For example, with reference to FIGS. 9a–c, the pump 100 may be modified to include an initial prime block 170 that is releasably mounted to the piston 106 as shown in FIG. 9a. The resiliency of the annular seal 148 may be relied upon to hold the initial prime block 170 relative to the piston 106. Also, an initial fluid-collecting chamber 172 is provided with an initial dose-control portion 174 which is preferably cylindrical having a diameter S and a height R. The dimensions S, R are selected so that the initial prime block 170 may be fixed therein upon being forced by the piston 106. Also, the dimensions S, R are selected to define a volume dose sufficiently large enough to obtain initial prime with one or more actuations of the pump 100, as needed.

The fluid-collecting chamber 136 and the dose-control portion 138 are defined within the initial prime block 170. To achieve initial prime with minimal actuations, the volume of the initial dose-control portion 174 will preferably be greater than the volume of the dose-control portion 138. A passage 176 extends from the dose-control portion 138 defined in the initial prime block 170 into communication with a check-valve chamber 178 having a check-valve element 180 (e.g., a check-valve ball) disposed therein.

In operation, with reference to FIG. 9a, the initial prime block 170 is mounted onto the piston 106 and spaced from the initial fluid-collecting chamber 172. Fluid from the reservoir 128 is pressure-fed into the initial fluid-collecting chamber 172 and, in particular, the initial dose-control portion 174. To facilitate the pressure feed, the initial fluid-collecting chamber 172 may be provided with tapered portions 173; also, fins 175 may be provided to limit off-center movement of the initial prime block 170. Upon initial actuation of the pump 100, initial stroke of the piston 106 is caused, and the piston 106 translates downwardly with the initial prime block 170 being forced into the initial fluid-collecting chamber 172, and more specifically into the initial dose-control portion 174. During such translation, as shown in FIG. 9b, the initial prime block 170 seals the initial dose-control portion 174 from the reservoir 128 and causes dosing of the fluid residing in the initial dose-control portion 174. The check-valve element 180 prevents fluid from escaping through the passage 176 and up into the dose-control portion 138. Due to the large volume of the initial dose-control portion 174, excessive fluid may be urged into and through the nozzle control chamber 152 achieving or substantially achieving full priming of the pump 100. Upon release of the cap 108, the piston 106 is urged upwardly, as described above, and out of the dose-control portion 138, as shown in FIG. 9c. As is readily evident, the holding force generated between the initial fluid-collecting chamber 172 and the initial prime block 170 must be greater than that generated between the piston 106 and the initial prime block 170. The operation of this variation of the pump 100 is generally the same as described above, except that the check-valve element 180 throttles the fluid displaced from the dose-control portion 138 en route to being dispensed via the nozzle 160.

Figure 10A:
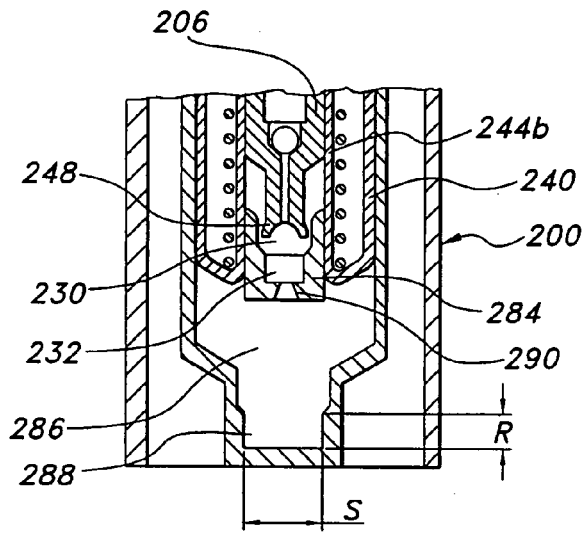
FIGS. 10a–10c are views showing placement of an initial prime block in causing initial prime for the second embodiment of the pump.
Figure 10B:
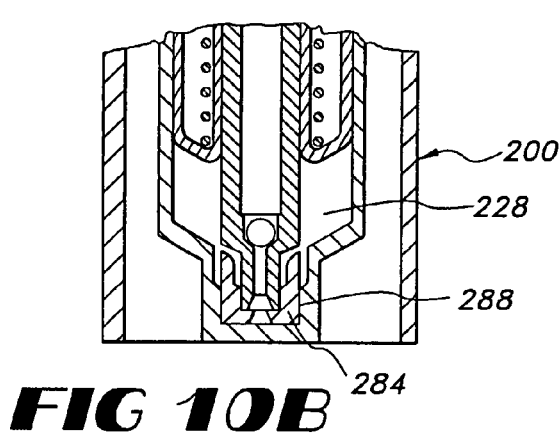
Figure 11:
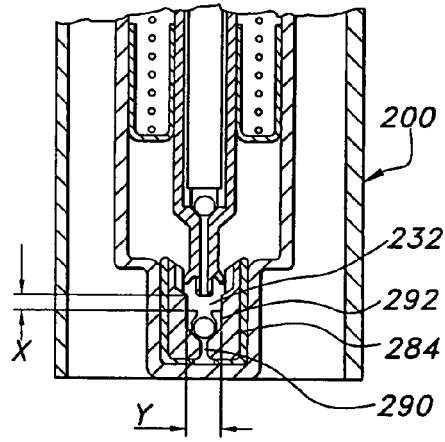
FIG. 11 shows a second version of an initial prime block usable with the second embodiment of the pump.
Figure 10C:
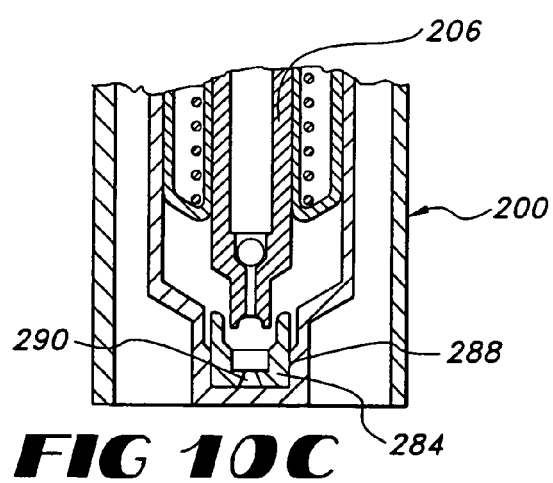

With reference to FIGS. 10a–10c and 11, an initial priming feature may also be provided for the pump 200. The initial prime block 284 is pressed into the expanded flange 244b of the pressure piston 240 so as to be relatively fixed thereto. The fluid-collecting chamber 230 and the dose-control portion 232 are defined within the initial prime block 284. The reservoir 228 is adapted to terminate in an initial fluid-collecting chamber 286 having an initial dose-control portion 288. As with other designs of dose-control portions, the initial dose-control portion 288 is preferably cylindrical with a diameter S and a height R. The initial prime block 284 is dimensioned to wedge into, and be fixed relatively to, the initial dose-control portion 288. Also, the volume encompassed by the initial dose-control portion 288 is such as to allow for full priming of the pump 200 upon a minimal number of actuations. A passageway 290, which may be tapered, extends through a bottom of the initial prime block 284 into communication with the dose-control portion 232. In use, upon initial actuation and downward translation of the piston 206, as shown in FIGS. 10a and 10b, the annular seal 248 engages the dose-control portion 232 and causes downward movement of the initial prime block 284. The initial prime block 284, upon entering the initial dose-control portion 288, causes it to be sealed from the reservoir 228 and fluid trapped therein to be pressurized. Fluid is forced through the passageway 290 and up into the piston 206 in a similar manner to that described above. The volume of the fluid defined by the initial dose-control portion 288 is greater than with a normal dose, so as to wet all surfaces and obtain proper prime with minimal actuations of the pump 200. Upon release of the cap 208, the piston 206 returns upwardly and releases from the initial prime block 284. The holding force between the initial dose-control portion 288 and the initial prime block must be greater than the holding force between the piston 206 and the initial prime block 284. Once primed, the pump 200 operates in a similar manner to that described above, although fluid will be trapped in the volume encompassed by the passageway 290.

As an additional variation, the initial prime block 284 may be formed with a check valve 292 located between the passageway 290 and the dose-control portion 232. The check valve allows for flow upwardly through the initial prime block 284 during priming, but prevents flow of fluid down into the passageway 290 during use.

Figure 12:
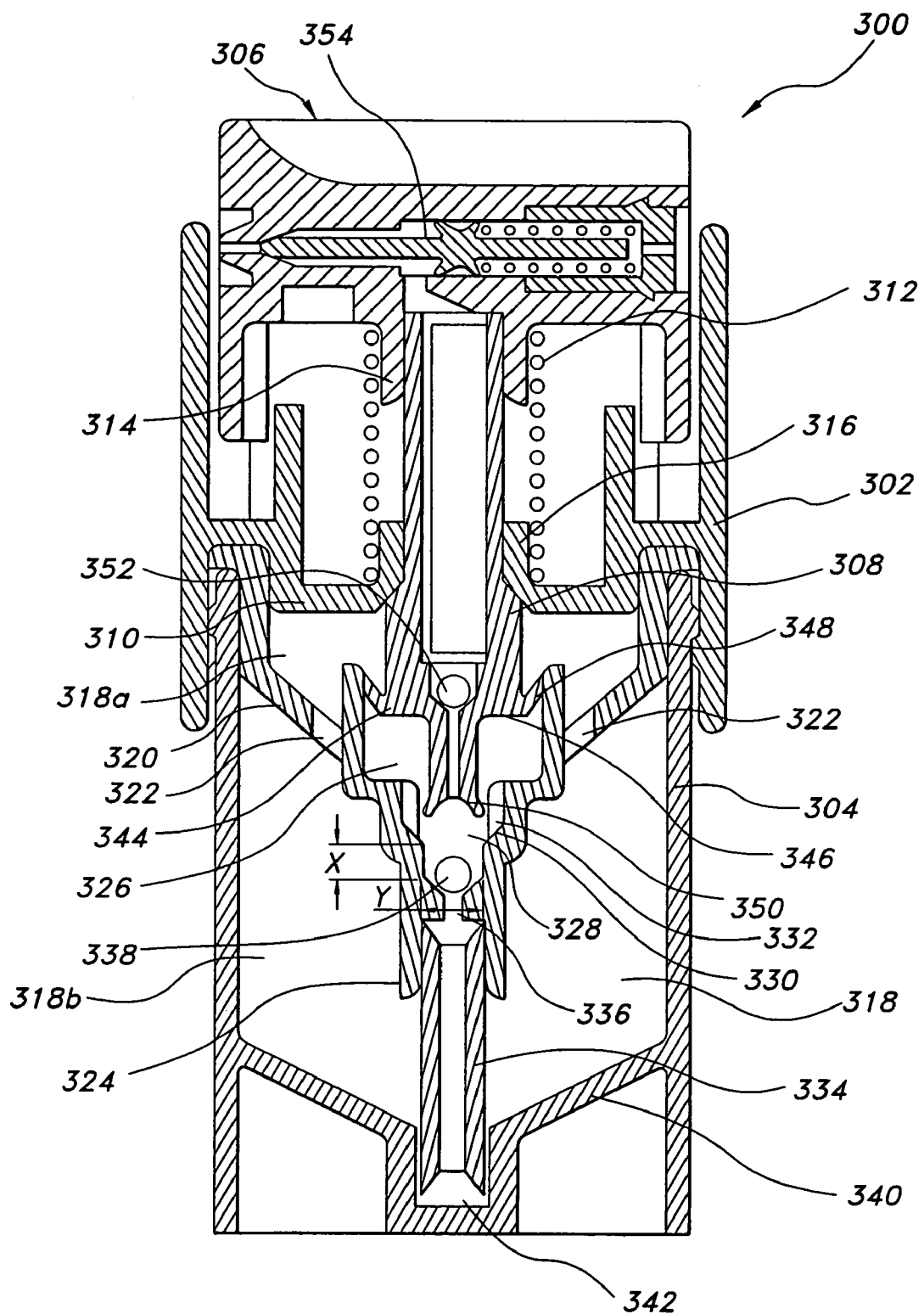
FIG. 12 is a schematic of the interior of a third embodiment of a pump formed in accordance with the subject invention.

With respect to FIG. 12, a third embodiment of the subject invention is depicted and generally designated with the reference numeral 300. Unlike the first and second embodiments of the subject invention, the pump 300 may be used as a true pump mountable onto any container or reservoir. The pumps 100 and 200 require reservoirs 128 and 229 which are formed to cooperate with the pistons 106 and 206, respectively, for actuation. The pump 300 does not need such a specially-formed reservoir.

The pump 300 includes a housing 302, a reservoir wall 304, and a cap 306 which is used to actuate the pump 300. The housing 302 is mounted to the reservoir wall 304 using any technique known to those skilled in the art, such as a snap-fit or threaded connection. A piston 308 is slidably disposed to extend through an end cover 310 which may be formed unitarily with, or separately from, the housing 302. A cap spring 312 is disposed between the end cover 310 and the cap 306 so as to urge the cap 306 upwardly and away from the end cover 310. An inner wall 314 depending downwardly from the cap 306 and/or a shoulder 316 extending from the end cover 310 may be provided to supply the cap spring 312 with columnar support. The specific structure of the cap 306 and its internal components are described above with respect to the previous embodiments. In addition, the locking mechanism described above (e.g., using the ribs 116; 216) may also be utilized with the subject embodiment.

The reservoir wall 304 defines a reservoir 318 which is divided into an upper reservoir chamber 318a and a lower reservoir chamber 318b by a divider 320. The upper and lower reservoir chambers 318a and 318b are in open fluid communication through holes 322. The divider 320 supports an inner wall 324 which defines an upper fluid-collecting chamber 326. The fluid-collecting chamber 326 reduces to a dose-control portion 328 defined by the dimensions X, Y. The wall 324 also terminates to hold a dip tube 334 that extends from the inner wall 324 into communication with the lower reservoir chamber 318b. The dip tube 334 is in communication with the dose-control portion 328 via an inlet aperture 336. A check-valve element 338 is seated in the dose-control portion 328 at the inlet aperture 336 to regulate flow into the dose-control portion 328. To optimally collect fluid at the bottom of the reservoir 318, a bottom wall 340, partially defining the reservoir 318, may be formed tapered to converge at a well 342 into which the dip tube 334 extends. The wall 324 alternatively could reduce diameter and continue down to eliminate the dip tube 334. As with the previous embodiments, tapered portions 330 and fins 332 may be provided to facilitate filling of the dose-control portion 328 and to limit off-center movement of the piston 308, respectively.

The piston 308 is formed similarly to the piston 206 described above with respect to the pump 200. Here, however, the piston 308 includes a secondary piston 344 defined by an end face 346 and a secondary annular seal 348. The secondary piston 344 is formed to seal the fluid-collecting chamber 326 from the upper reservoir chamber 318a.

In operation, downward depression of the cap 306 results in an annular seal 350 of the piston 308 entering the dose-control portion 328 and causing pressurization of fluid disposed therein. The check-valve element 338 prevents fluid escape through the inlet aperture 336 during such pressure build-up. Upon sufficient pressure build-up, fluid will cause inner check-valve element 352 to be lifted, causing open communication between the dose-control portion and nozzle control chamber 354. Administration of a fluid dose is achieved in the same fashion as described above with respect to the other embodiments. Upon fluid discharge, and release of the cap 306, the cap 306 is urged to its natural resting position, as shown in FIG. 12, with the piston 308 being retracted from the dose-control portion 328. Upon such retraction, the secondary piston 344 creates a suction effect within the fluid-collecting chamber 326, causing the check-valve element 338 to be lifted and fluid to be drawn into at least the dose-control portion 328. It is preferred that a volume of fluid greater than the dose-control portion 328 be drawn into the fluid-collecting chamber 326, thereby assuring full filling of the dose control 328. Once sufficient fluid has been drawn, and pressure sufficiently increases, the check-valve element 338 returns to its seated position. During actuation, any excess fluid in the dose-control portion 328 will be forced about the secondary annular seal 348 and into the upper reservoir chamber 318a.

As will be recognized by those skilled in the art, pumps formed in accordance with the subject invention can use different piston configurations to create various pressure differentials for urging fluid from the reservoir, such as fluid urged from the reservoir under pressure, suction, or a combination thereof. With respect to FIG. 13, a fourth embodiment of the subject invention is depicted and generally designated with the reference numeral 400. As with the third embodiment of the subject invention, the fourth embodiment relies on suction for urging fluid from the reservoir.

With the pump 400, a housing 402, and a cap 406 are provided formed generally in accordance with the same principles as described above. A piston 408 is rigidly mounted to the cap 406 so as to move in concert therewith. The piston 408 includes a ram portion 410 about which is defined an annular seal 412. A reservoir wall 404 defines a reservoir 414 that is separated into an upper reservoir chamber 414a and a lower reservoir chamber 414b by a divider 416. The upper and lower reservoir chambers 414a and 414b are in fluid communication via a passageway 418. The divider 416 is formed with a cup-shaped well 420 that is in open fluid communication with the upper reservoir chamber 414a. The well 420 defines a fluid-collecting chamber 422 which converges and terminates in a dose-control portion 424 that is defined by the dimensions X, Y. The annular seal 412 is formed to bear against and define a seal with the well 420 in the dose-control portion 424. In addition, the piston 408 is formed with a secondary piston 426 having a peripheral annular seal 427 that bears against and defines a seal with the reservoir wall 404 in the upper reservoir chamber 414a. As with the pump 300, the piston 408 preferably draws a greater volume of fluid than the dose-control portion 424 to assure compete filling thereof.

The piston 408 includes a passageway 430 that terminates in an inner check-valve chamber 432 in which is seated a check-valve element 434. A bore 436 extends therefrom into communication with a nozzle control chamber 438. The formation of the bore 436 and the elements within the cap 406 are as with the previous embodiments.

To achieve actuation, the piston 408 is forced downwardly with downward depression of the cap 406 resulting in eventual bottoming of the annular seal 412 against the bottom of the well 420. Tapered surface 440 may be provided to gradually contract the annular seal 412 with downward descent of the piston 408. Consequently, fluid trapped within the dose-control portion 424 is pressurized and forced up through the bore 436 to be dispensed from the pump 400. Upon release of the cap 406, and upward movement of the piston 408 caused by cap spring 442, the secondary piston 426 creates a suction effect within the upper reservoir chamber 414a which draws fluid from the lower reservoir chamber 414b into the dose-control portion 424 via the fluid-collecting chamber 422.

Figures 13, 13A:
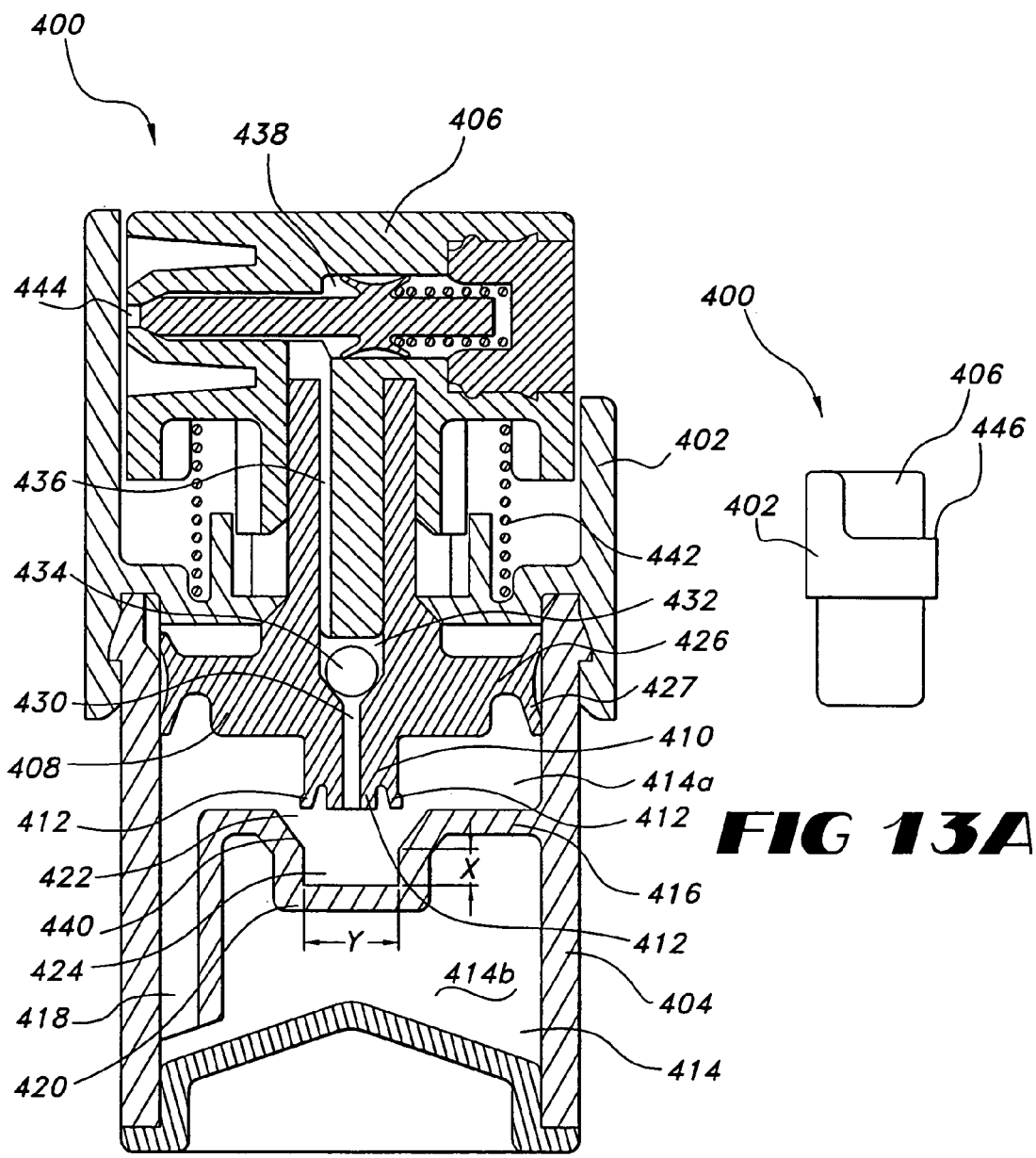
FIG. 13 is a schematic of the interior of a fourth embodiment of a pump formed in accordance with the subject invention.
FIG. 13a is a side elevational view of a pump with a set-back.

It should also be noted that the housing 402 may be formed with a set-back 446 such that the cap 406 is exposed in a rest position yet fully shielded by the housing 402 in proximity to nozzle 444 (FIG. 13a).

Figure 14:
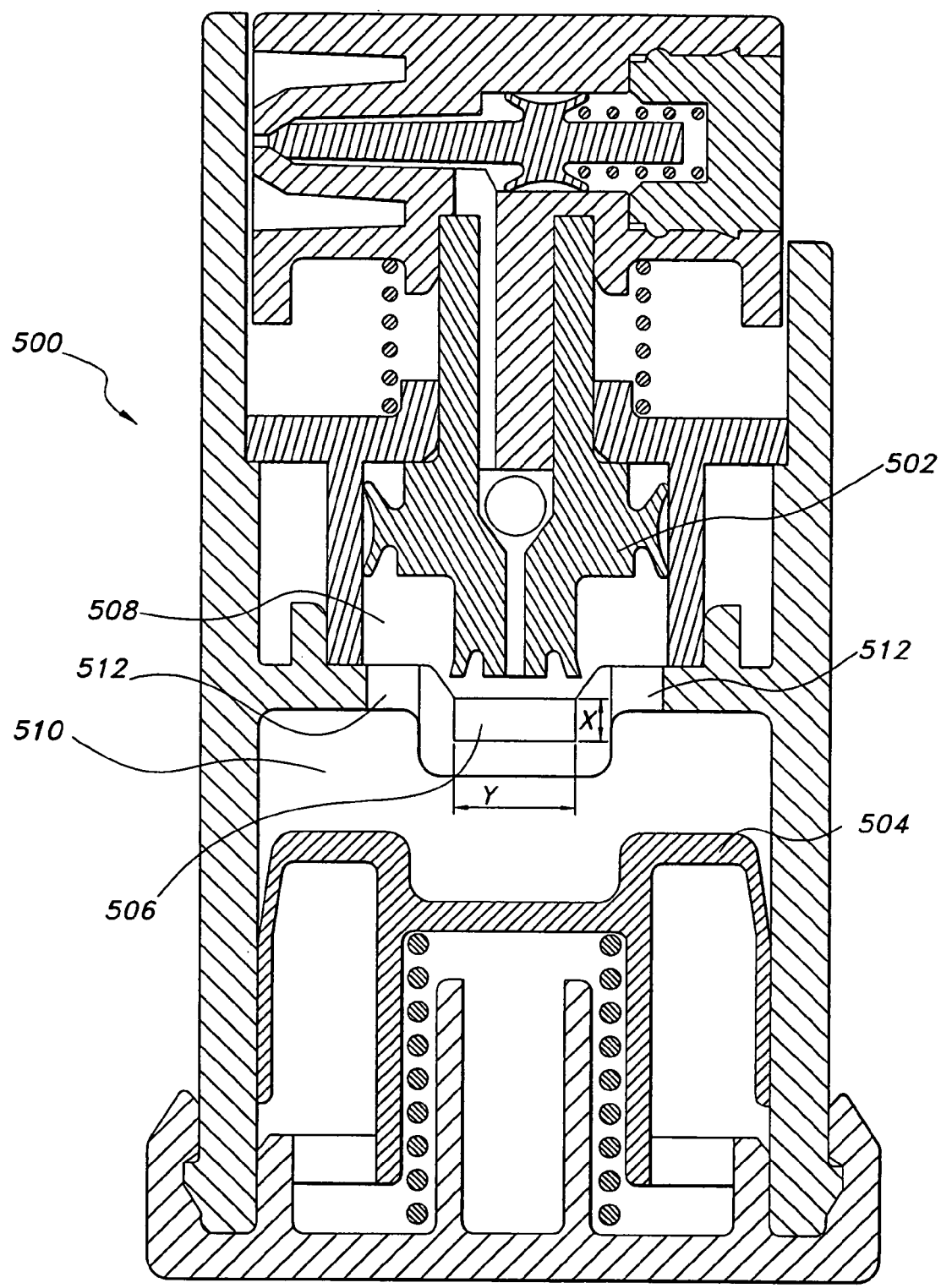
FIG. 14 is a schematic of the interior of a fifth embodiment of a pump formed in accordance with the subject invention.

With respect to FIG. 14, a fifth embodiment of the subject invention is depicted and generally designated with the reference numeral 500. Here, the pump 500 is provided with a piston 502 formed in accordance with the fourth embodiment of the subject invention. In addition, a pressure piston 504 is provided for urging fluid under pressure into a dose-control portion 506 via a fluid-collecting chamber 508 from reservoir 510 through holes 512. The dose-control portion 506 is formed with dimensions X, Y. The pump 500 basically operates the same as the pump 400, except that the pressure piston 504 aids in urging fluid from the reservoir 510, in addition to suction generated by the piston 502.

Figure 15:
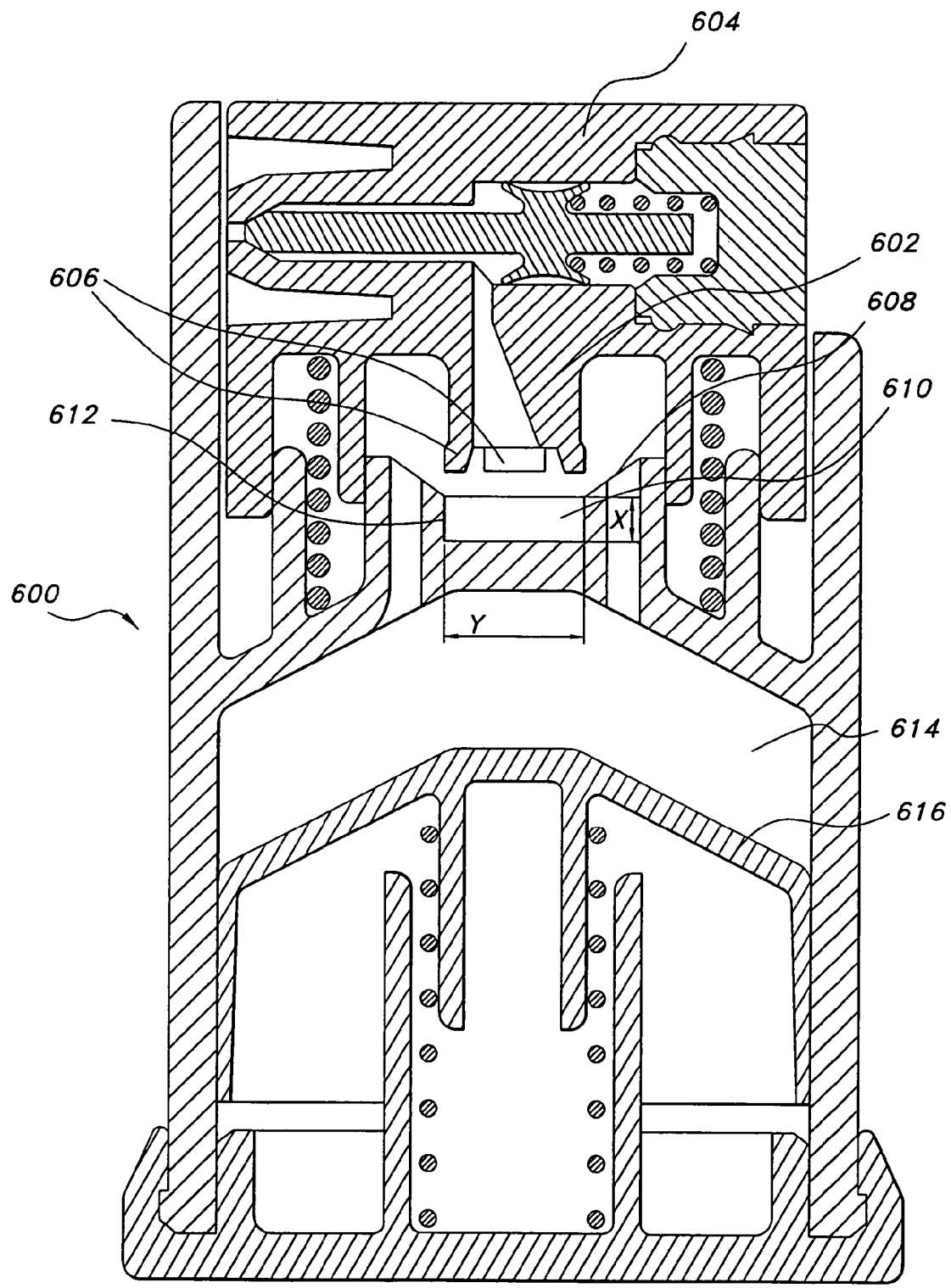
FIG. 15 is a schematic of the interior of a sixth embodiment of a pump formed in accordance with the subject invention.

In a sixth embodiment of the subject invention, as shown in FIG. 15, a pump 600 is provided similar to the fifth embodiment. Here, however, piston 602 of the subject embodiment extends from cap 604 and is formed with an annular seal 606 that is inwardly deflected upon engaging tapered surface 608. In this manner, the annular seal 606 is urged into dose-control portion 610 with the piston 602 translating downwardly to bear against wall 612 to form a seal therewith. Also, fluid is urged from reservoir 614 to replenish the dose-control portion 610 only under pressure from pressure piston 616. In all other respects, the pump 600 is formed and operated in accordance with the disclosures above.

As a further variation, pumps can be formed in accordance with the subject invention where the dose-control portion and the fluid-collecting chamber are formed with generally the same width, thus avoiding a reduction in diameter of the piston upon entry into the dose-control portion. For example, with reference to FIG. 16, a seventh embodiment of the subject invention is depicted and generally designated with the reference numeral 700. With the present embodiment, end cover 702 is provided with an upstanding inner wall 704 which encircles, and partially defines, a fluid-collecting chamber 706. An inlet aperture 708 is defined which communicates with the fluid-collecting chamber 706 and a reservoir 710.

A piston 712 is slidably disposed within the fluid-collecting chamber 706 which has an annular seal 714 in bearing engagement against the inner wall 704 to form a seal therewith. The piston 712 also includes a ram portion 716 that encircles a passageway 718. The passageway 718 is in fluid communication with an inner check-valve chamber 720, and the ram portion 716 is preferably formed with a generally flat face 722. A shoulder 724 protrudes from the end wall 702 so as to at least partially bound the inlet aperture 708. A check-valve element 726 is disposed within the shoulder 724 to be seated at the inlet aperture 708 to regulate flow therethrough. Likewise, an inner check-valve element 728 is disposed within the inner check-valve chamber 720 to regulate flow thereinto.

Figure 16:
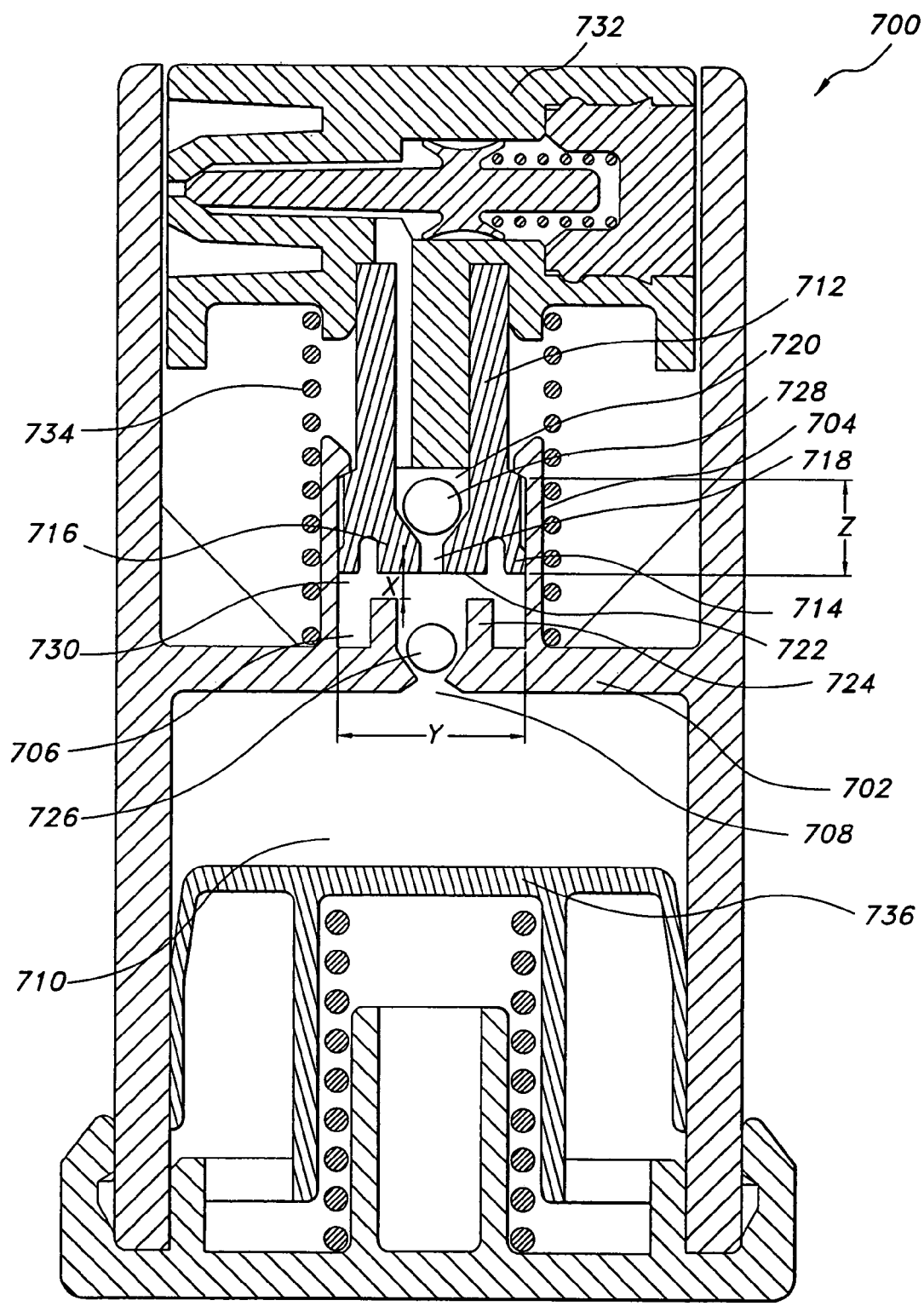
FIG. 16 is a schematic of the interior of a seventh embodiment of a pump formed in accordance with the subject invention.

With the subject invention, a dose-control portion 730 of the fluid-collecting chamber 706 is defined between the shoulder 724 and the piston 712. Particularly, the dose-control portion 730 has a height X between the shoulder 724 and the piston 712, and a diameter Y equal to the inner diameter of the inner wall 704. In contrast to the majority of the other embodiments, dosing of the pump 700 is a function of three dimensions, not two. With reference to FIG. 16, the dimension Z defines the upper end of the stroke of the piston 712, and, thus, is implicated in defining the dimension X. As such, dosage volume is a function of the dimensions X, Y and Z. With the majority of the other embodiments, dosage is a function of two dimensions X and Y.

In operation, the piston 712 is downwardly driven in concert with cap 732. Upon such downward translation, fluid entrapped between the piston 712 and the shoulder 724 is pressurized, eventually resulting in the inner check-valve element 728 being lifted to allow for dose administration as described above. The stroke of the piston 712 is limited by interengagement of the face 722 against the shoulder 724. Upon upward movement of the piston 712 to return to its rest position under force of cap spring 734, the piston 712, due to the annular seal 714 forming a seal with the inner wall 704, creates suction to lift the check-valve element 726 from the inlet aperture 708 to draw fluid from the reservoir 710 into the fluid-collecting chamber 706. With sufficient fluid having been urged into the fluid-collecting chamber 706, the check-valve element 726 returns to its seated position to seal the dose-control portion 730 from the reservoir 710. Pressure piston 736 also bears against fluid in the reservoir 710 to pressurize it in urging fluid from the reservoir 710 as needed.

Figure 17:
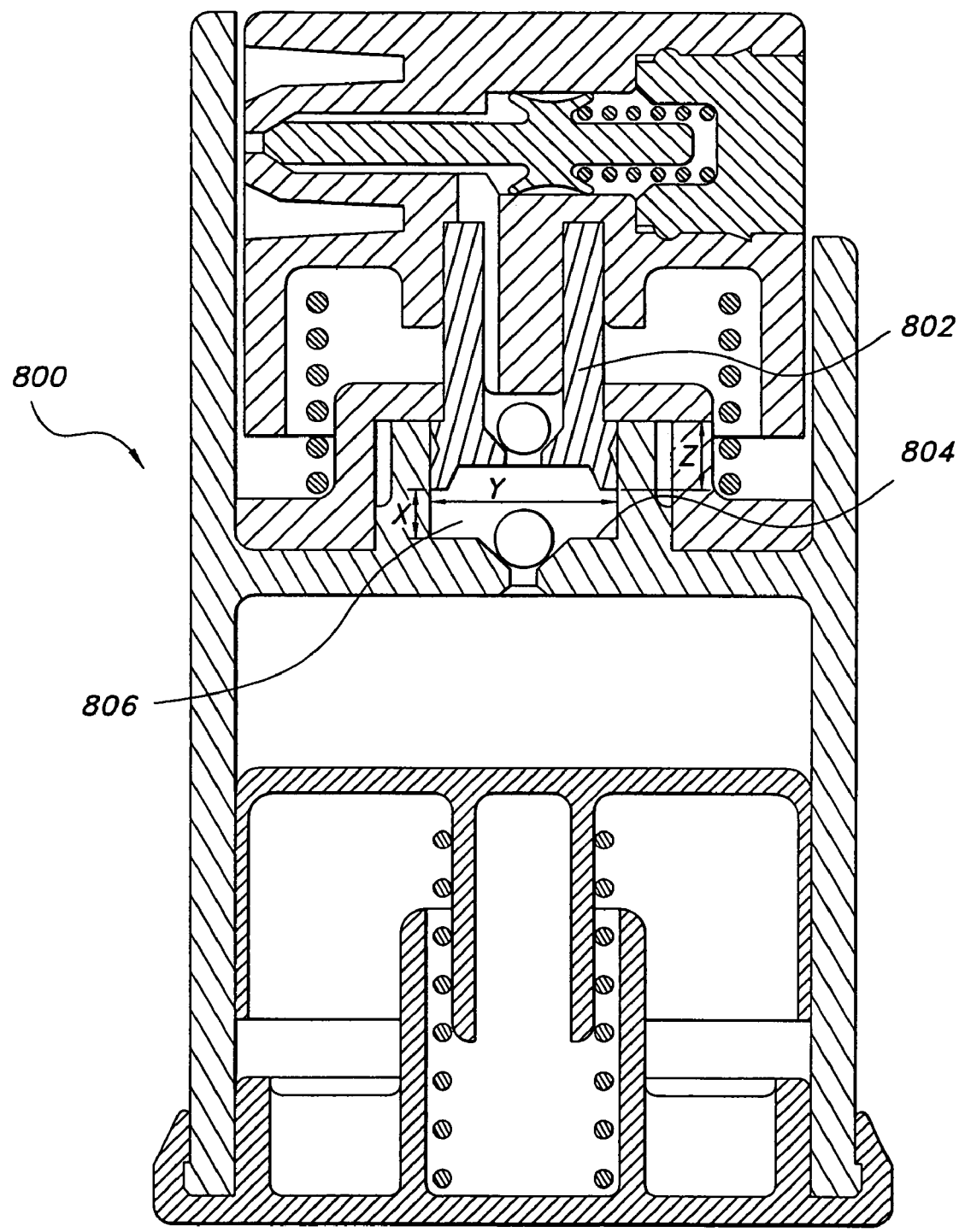
FIG. 17 is a schematic of the interior of an eighth embodiment of a pump formed in accordance with the subject invention.

FIG. 17 depicts an eighth embodiment of the subject invention which is generally designated with the reference numeral 800. The pump 800 is very similar to the pump 700, except that piston 802 is formed to bottom out at end wall 804 instead of on a shoulder as with the seventh embodiment. Accordingly, a dose-control portion 806 is defined with dimensions X, Y as shown in FIG. 17. As with the pump 700, the dimension Z defines stroke length and has an effect on dosage volume.

As also will be appreciated by those skilled in the art, a pump can be formed in accordance with the subject invention having the dose-control portion defined within the cap. For example, with reference to FIG. 18, a ninth embodiment of the subject invention is depicted and generally designated with the reference number 900. The pump 900 includes a housing 902 and a cap 904 for actuating the pump 900. The cap 904 includes internal components as described above. An end cover 906 extends across the housing 902 from which protrude upwardly an upstanding wall 908 and a piston 910. In contrast to previous embodiments, the piston 910 is stationary.

The cap 904 is formed with a downward depending inner wall 912 that terminates in an annular seal 914 which bears against the wall 908 to form a seal therewith. A fluid-collecting chamber 916 is defined between the wall 908, the piston 910, and the inner wall 912 which terminates in a dose-control portion 918 defined in the cap 904. The dose-control portion 918 is formed with the dimensions X, Y. The piston 910 includes an annular seal 920 which is defined to be received within the dose-control portion 918 and to form a seal against the surrounding portions of the cap 904. Preferably, a tapered surface 921 is defined about the dose-control portion 918 in registration with the annular seal 920 such that the tapered surface 921 urges the annular seal 920 inwardly into the dose-control portion 918 during actuation as described below.

Figure 18:
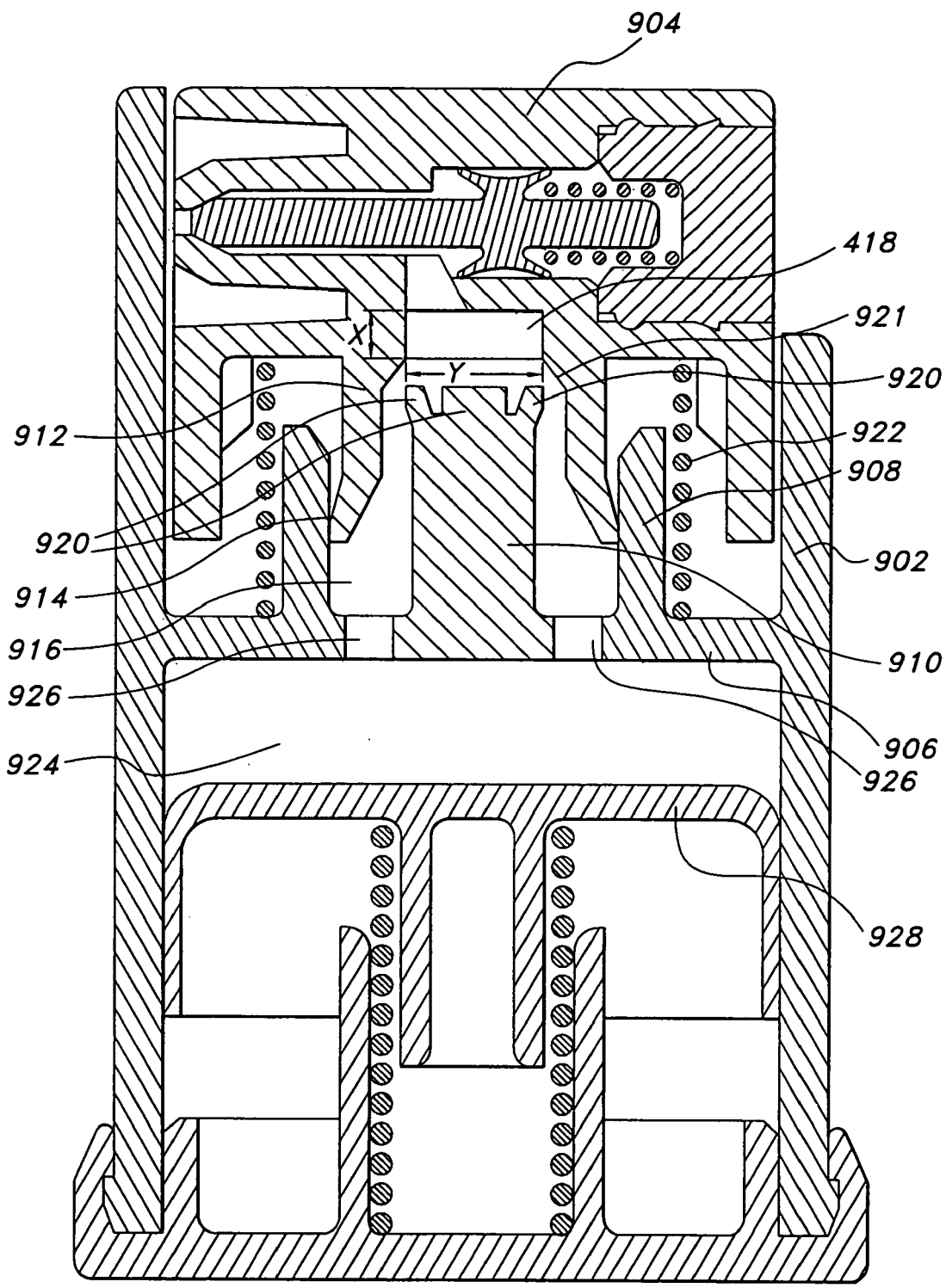
FIG. 18 is a schematic of the interior of a ninth embodiment of a pump formed in accordance with the subject invention.

In use, the cap 904 is caused to be downwardly translated, with the piston 910 eventually entering the dose-control portion 918 to pressurize fluid therein. Pressurized fluid is dispensed from the cap 904 in the same manner as described with previous embodiments. Upon release of the cap 904, cap spring 922 causes the cap 904 to return to its rest position, as shown in FIG. 18. Fluid is urged from reservoir 924 via holes 926 under suction resulting from retraction of the inner wall 912 in the fluid-collecting chamber 916, as well as, pressure generated by pressure piston 928 acting against fluid within the reservoir 924.

Figure 19:
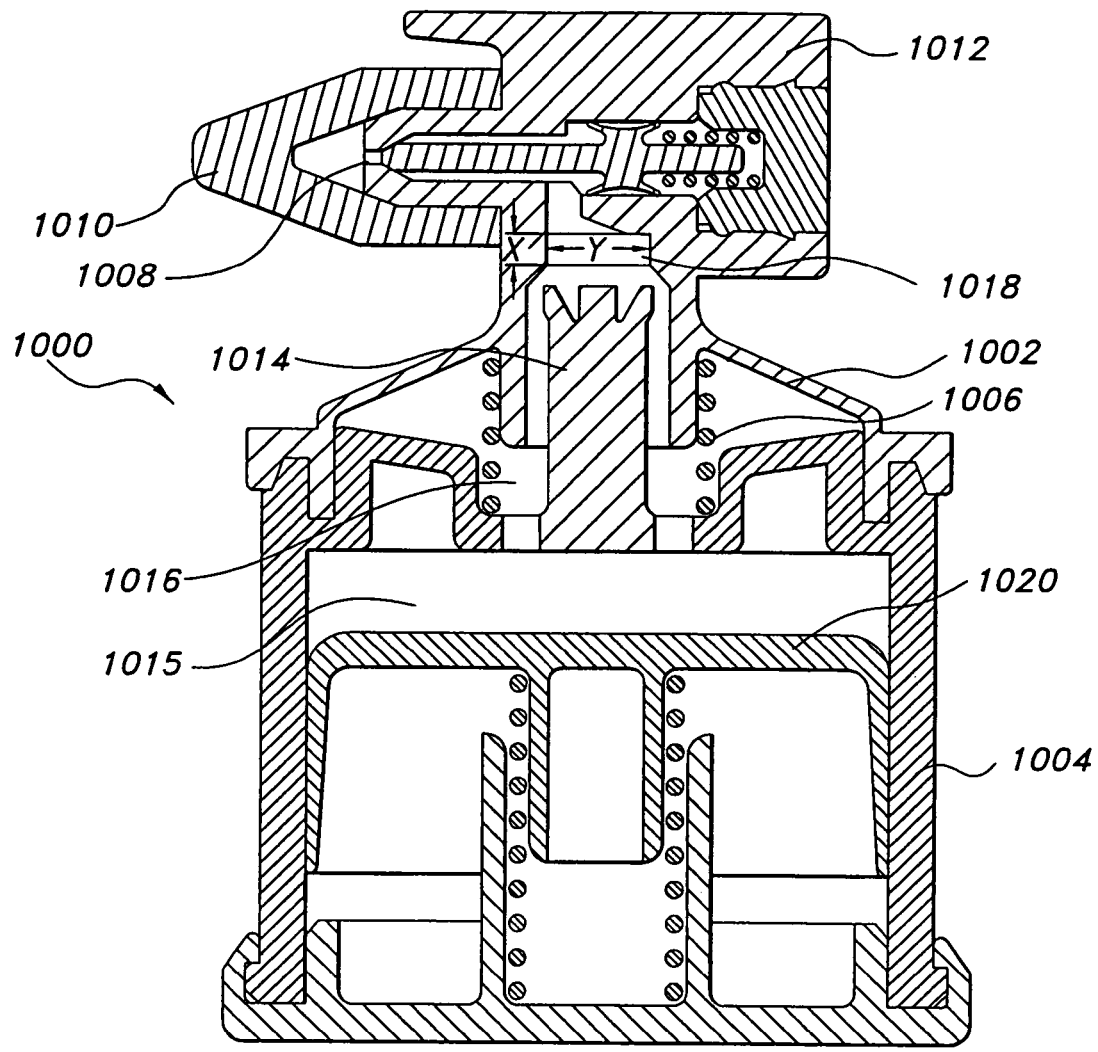
FIG. 19 is a schematic of the interior of a tenth embodiment of a pump formed in accordance with the subject invention.
Figure 19A:
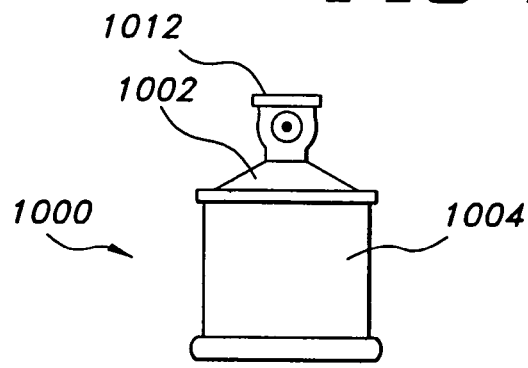
FIG. 19a is a front elevational view of the pump of the tenth embodiment.

With reference to FIGS. 19 and 19a, a tenth embodiment of the subject invention is depicted and generally designated with the reference numeral 1000. The tenth embodiment shows a pump formed in accordance with the subject invention that is sealed to limit ingress of contaminants thereinto. In particular, the pump 1000 includes a deflectable member 1002 which is attached to housing 1004 so as to define a tight seal therewith. Any technique known to those skilled in the art may be used to attach deflectable member 1002, such as ultrasonic welding. The deflectable member 1002 is preferably formed of resilient material. A cap spring 1006 applies a biasing force against the deflectable member 1002 to urge it into an upward position. With the deflectable member 1002, the pump 1000 may be hermetically sealed with only one opening to atmosphere, that being through nozzle 1008. An overcap 1010 may be removably mounted to cap 1012 to limit the ingress of contaminants through the nozzle 1008.

In basic respects, the pump 1000 operates in the same manner as the pump 900. Upon actuation, the deflectable member 1002 deflects downwardly with the cap 1012 to allow for administration of fluid by piston 1014. Upon returning to its rest position, suction is generated by the deflectable member 1002. Fluid is urged from reservoir 1015 into fluid-collecting chamber 1016 and dose-control portion 1018 by both suction generated by the deflectable member 1002 and pressure generated by pressure piston 1020.

Figure 20:
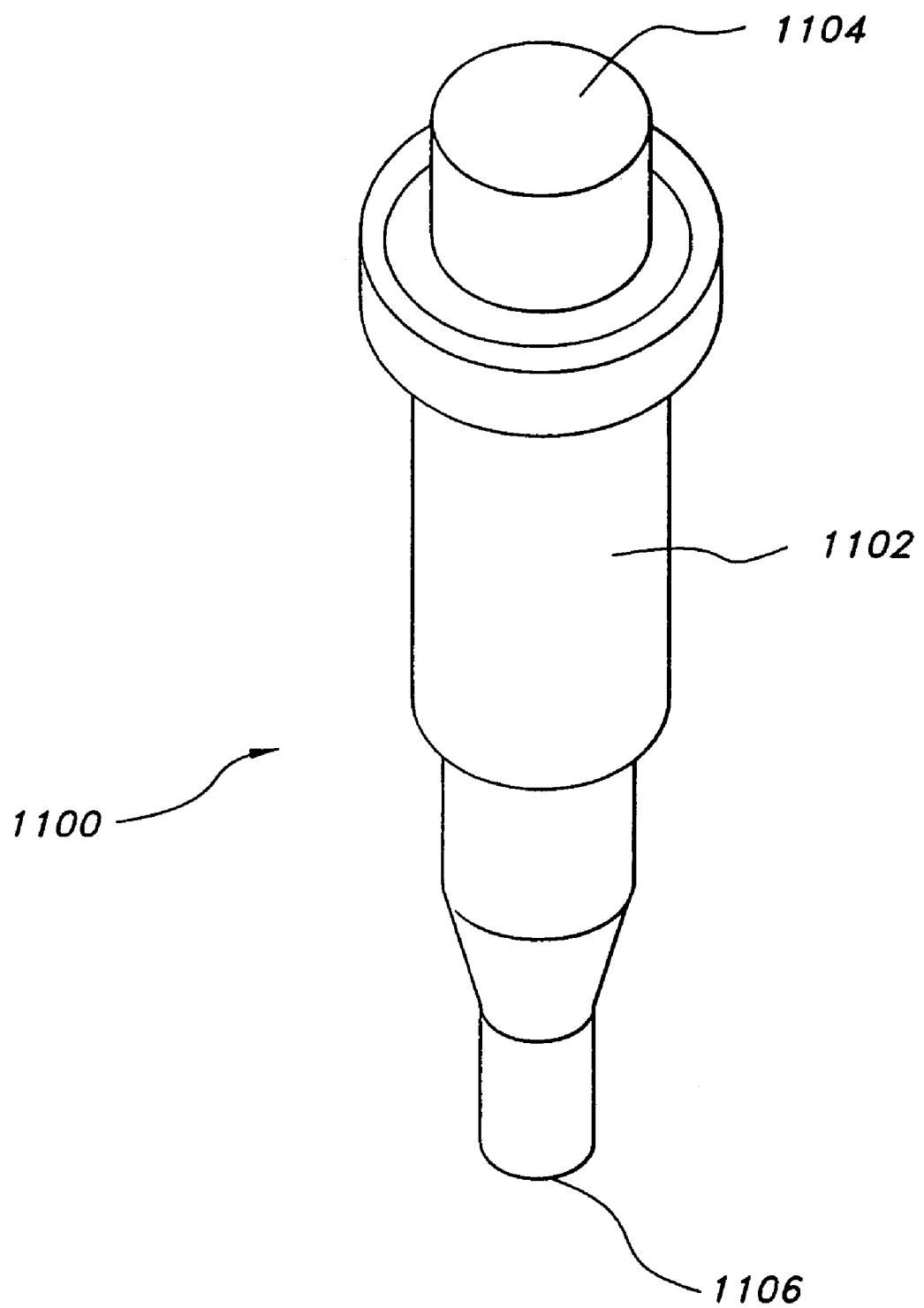
FIG. 20 is a perspective view of an eleventh embodiment of a pump formed in accordance with the subject invention.

As also will be appreciated by those skilled in the art, various pump configurations may be utilized in accordance with the principles of the subject invention. The previous embodiments were generally described in relation to a pump which dispenses in a direction transverse to the direction of pump actuation (in other words, fluid is dispensed in a direction transverse to the direction in which the cap is depressed to cause actuation). In addition, a pump can be formed in accordance with the subject invention in which fluid is dispensed "in-line" with the actuation direction. With reference to FIG. 20, an eleventh embodiment of the subject invention is depicted and generally designated with the reference numeral 1100. The pump 1100 generally includes a housing 1102 having at one end cap 1104, for actuating the pump 1100, and at another end nozzle 1106 for dispensing fluid.

Figure 21:
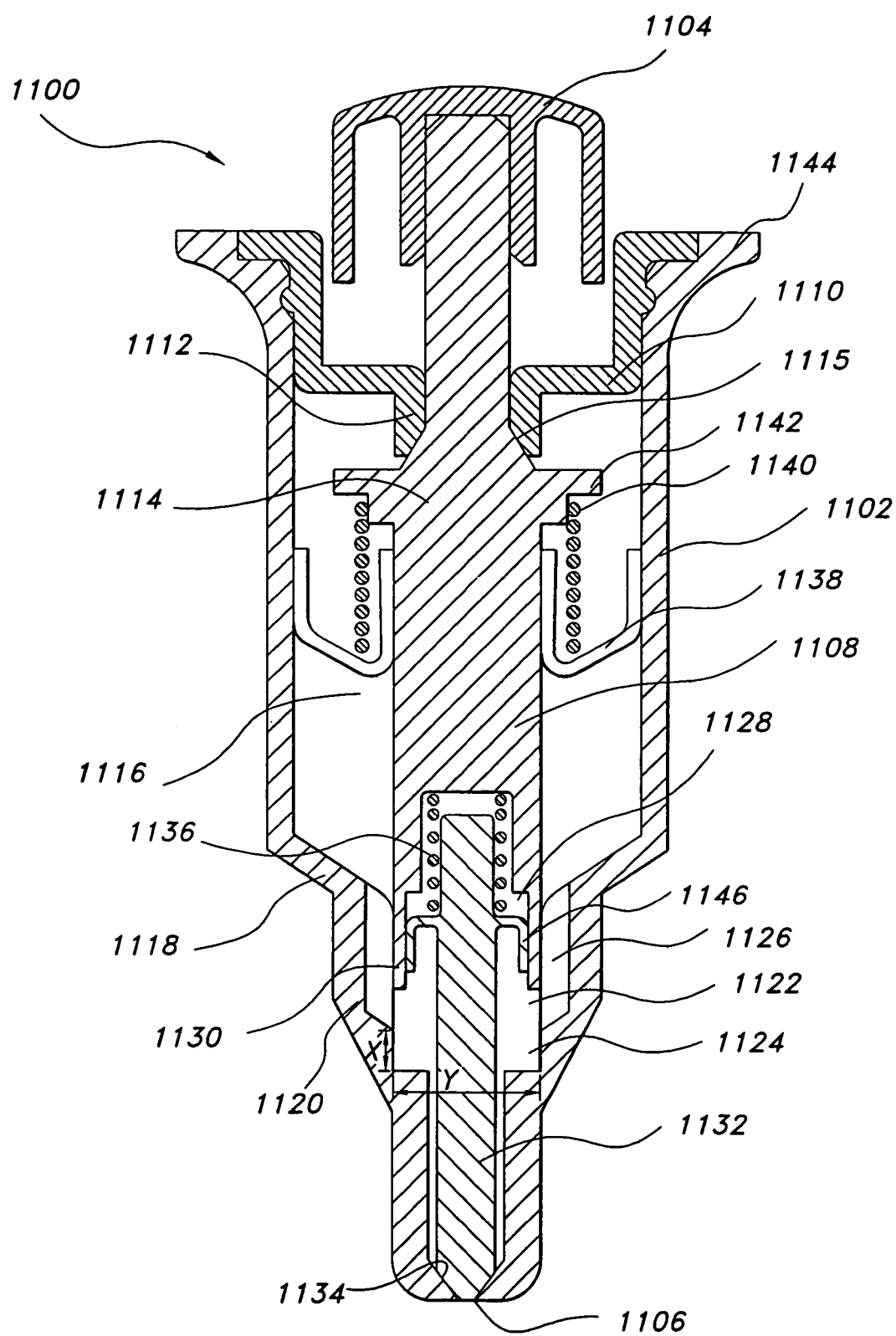
FIG. 21 is a schematic of the interior of the pump of the eleventh embodiment.

With reference to FIG. 21, a piston 1108 is rigidly mounted to the cap 1104 which is slidably disposed through an end cover 1110. The end cover 1110 is preferably formed separately from the housing 1102 and is mounted thereto using any technique known to those skilled in the art, such as a snap-fit or a threaded connection. A shoulder 1112 depends downwardly from the end cover 1110 to engage an enlarged portion 1114 of the piston 1108 to limit upward movement thereof. Tapered section 1115 acts as a seal against the shoulder 1112 in a rest position.

A reservoir 1116 is defined about the piston 1108 and within the housing 1102. The housing 1102 includes a tapered section 1118 that converges to a well 1120 that defines a fluid-collecting chamber 1122. The well 1120 also defines a dose-control portion 1124 having dimensions X, Y. Preferably, fins 1126 are defined within the well 1120 to limit off-center movement of the piston 1108, yet allow fluid to be urged from the reservoir 1116 into the fluid-collecting chamber 1122 about the piston 1108.

The piston 1108 includes a recessed section 1128 which is bound by an annular seal 1130. The annular seal 1130 is formed to slide within the dose-control portion 1124 and form a seal with the surrounding portions of the well 1120. A nozzle piston 1132 is partially disposed within the recessed section 1128 which is urged away from the piston 1108 into bearing engagement with tapered surface 1134 by nozzle piston spring 1136. In a normal rest position, as shown in FIG. 21, the nozzle piston 1132 closes off the nozzle 1106.

A pressure piston 1138 is also provided which is urged into engagement with any fluid residing in the reservoir 1116 by push spring 1140 which bears against a collar 1142 formed on the piston 1108.

To facilitate actuation of the pump 1100, flanges 1144 may be formed on the housing 1102 adapted to be engaged by the pointer and middle fingers of an operator, allowing for thumb actuation of the cap 1104. As such, the pump 1100 may have a syringe-like action such as with known nasal sprayers.

In operation, the cap 1104 is depressed, resulting in downward translation of the piston 1108. The nozzle piston spring 1136 and the push spring 1140 will resist such downward translation, but will not prevent such. Upon sufficient downward translation, the annular seal 1130 enters the dose-control portion 1124 to pressurize fluid entrapped therein. Upon sufficient fluid build-up, the fluid will act against nozzle flange 1146 (which forms a seal with the annular seal 1130) to cause compression of the nozzle piston spring 1136 and, thus, separation of the nozzle piston 1132 from the tapered surface 1134. Pressurized fluid is then dispensed from the nozzle 1106. Upon sufficient pressure decay, the nozzle piston 1132 is returned to its rest position. With release of the cap 1104, the nozzle piston spring 1136 (with the nozzle piston 1132 bearing against the tapered surface 1134) acts against the piston 1108 to push it upwardly to its rest position. As the piston 1108 is withdrawn from the dose-control portion 1124, suction is generated which urges fluid from the reservoir 1116 thereinto. In addition, with the piston 1108 being in its rest position, the push spring 1140 urges the pressure piston 1138 to bear against fluid within the reservoir 1116 so as to pressurize the fluid therein.

Other embodiments of the "in-line" pump are possible in accordance with the subject invention. For example, with reference to FIG. 22, a twelfth embodiment of the subject invention is depicted and generally designated with the reference numeral 1200. The pump 1200 includes many of the same elements of the pump of the eleventh embodiment. Here, in contrast to the eleventh embodiment, an additional return spring 1202 is provided which acts against a collar 1204 to urge piston 1206 to a rest position. In addition, push spring 1208, which acts on pressure piston 1210, bears against end cover 1212, rather than the piston 1206. Slots 1207 may be provided which allow fluid to collect between the piston 1206 and nozzle piston 1209 so as to generate low fluid pressure acting against the nozzle piston 1209. In all other respects, the pump 1200 is generally the same as the pump 1100 of the eleventh embodiment and operates in the same manner.

Figures 22, 23:
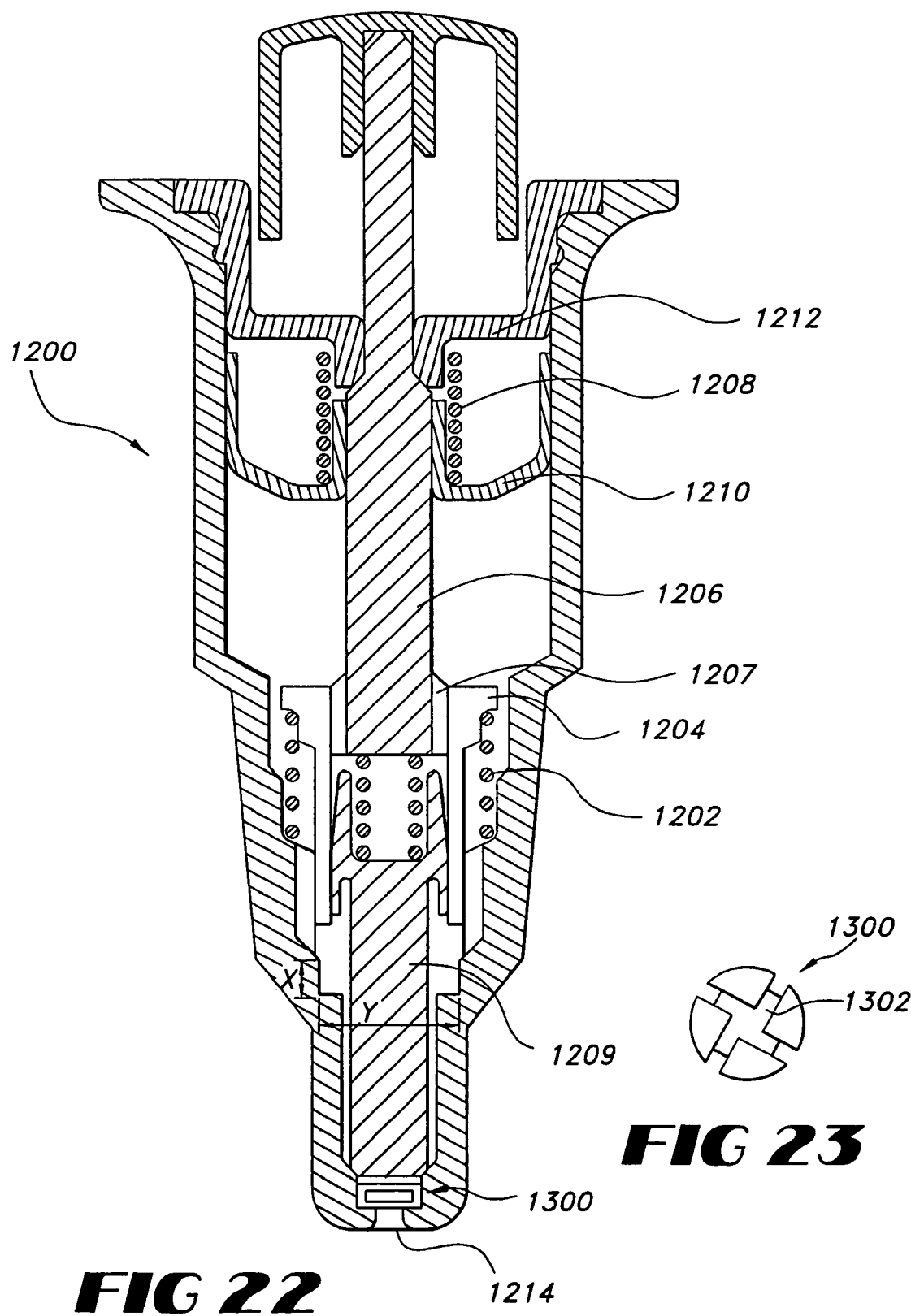
FIG. 22 is a schematic of the interior of a twelfth embodiment of a pump formed in accordance with the subject invention.
FIG. 23 is a top plan view of a spray plug.

As an additional feature, a conventional spray plug 1300 may be used with either of the embodiments to provide for spray discharge of a dose. Various spray plug configurations are known in the prior art. As an exemplary embodiment, as shown in FIG. 23, the spray plug 1300 may include radiating channels 1302. When fluid goes through the channels 1302 and into the center of the plug 1300 where a swirling motion is imparted to the discharging fluid, causing the fluid to break up into a spray pattern. As shown in FIG. 22, the spray plug 1300 is located adjacent to nozzle 1214. To allow for diffuse administration, the nozzle 1214 may be formed to diverge.

As can be seen from the various embodiments of the subject invention, only two dimensions are used to define the dose-control portion and, thus, a minimal number of tolerances are implicated in controlling the dosing of the pump, providing for highly accurate control of dosing. With typical prior art pumps, five to twelve dimensions are implicated in controlling dosing amount, with each dimension having its own set of manufacturing tolerances. Having the dose-control portion of the various embodiments described above being cylindrical (X—height; Y—diameter), the volume of the dose-control portion can be accurately controlled. To illustrate the minimal tolerance effect of the formation of the dose-control portion in relation to dosing with the subject invention, exemplary tolerance ranges are provided. The following calculations are based on a cylindrical dose-control portion having a diameter Y, a height X, and a dose volume of 10 microliters. Since the volume of the dose of the pump is generally equal to the volume of the dose-control portion, to provide for dosing of 10 microliters, the encompassed volume of the dose-control portion is 10 microliters.

The following formula converts a volume measured in cubic inches to liters (where the dimensions X and Y are taken in inches):

$$\pi(Y/2)^2 \times (0.01639) = \text{volume in microliters}$$

where 0.01639 is a unit conversion factor.

With the dimensions X and Y having dimensional tolerances of +/−0.001 inches, Table 1 sets forth possible dose tolerances for a 10 microliter dose associated with different combinations of X and Y dimensions.

TABLE 1

| Y (in) | Y/2 (in) | X (in) | Max. Dose Vol. (μl) | Min. Dose Vol. (μl) | Max./Min. Dose Variation Range (μl) | Dose Tolerance (±μl) |
|---|---|---|---|---|---|---|
| .060 | .030 | .21579 | 10.384 | 9.625 | .76 | ±.38 |
| .080 | .040 | .12138 | 10.334 | 9.670 | .66 | ±.33 |
| .100 | .050 | .07768 | 10.332 | 9.674 | .66 | ±.33 |
| .120 | .060 | .05394 | 10.347 | 9.649 | .70 | ±.35 |
| .130 | .065 | .04597 | 10.376 | 9.633 | .74 | ±.37 |
| .140 | .070 | .03963 | 10.398 | 9.608 | .79 | ±.4 |
| .160 | .080 | .03035 | 10.460 | 9.562 | .90 | ±.45 |

As can be seen, tolerances as low as +/−0.33 microliters can be obtained. In contrast, prior art pumps have dose tolerances in the range of 3 to 5 microliters. As is readily apparent, the subject invention can provide for much more accurate dose control than with prior art devices.

Pumps of the subject invention can also be manufactured economically using multi-cavity molding. It is envisioned that 32 to 64 cavity molds will be particularly useful. Due to the two dimensions of the dose-control portion, a single core pin can be used to define the dose-control portion. Core pin tolerances can be held tightly during manufacture and as such do not greatly cause variations in the X and Y dimensions. Shrinkage of the constituent material will also cause variations in the X and Y dimensions. However, with small dimensions, less shrinkage effect is present.

Additionally, the subject invention avoids the phenomenon of "suck back" found in prior art pumps. With prior art pumps, upon discharge, a slight vacuum is typically formed within the nozzle which causes undispensed fluid to be drawn back therein, along with contaminants from the surrounding environment. The subject invention avoids this phenomenon by having fluid administered under positive pressure (i.e., fluid is pressurized upon release) and the nozzle piston returning to its closed, sealed position prior to further fluid being drawn into the nozzle control chamber. Accordingly, no vacuum is formed in the nozzle control chamber that directly communicates with the outside atmosphere. With avoidance of the introduction of contaminants, fluids contained within a pump formed in accordance with the principles of the subject invention need not be resistant to contaminants. For example, ophthalmic fluid medications can be stored by and dispensed with the subject pumps without preservatives.

In another aspect of the subject invention, an adapter 1400 may be provided for mounting onto any pump which dispenses in a direction transverse to the direction of pump actuation (in other words, the adaptor 1400 is for use with embodiments other than "in-line" pumps). With reference to FIGS. 24–27, the adapter 1400 is shown in conjunction with the pump 100 for illustrative purposes. The adapter 1400 can be used with other embodiments of the subject invention and other pumps.

The adapter 1400 includes a generally cylindrical body 1402 from which extends spaced-apart arms 1404. Elongated slots 1406 are defined through portions of the body 1402 and the arms 1404. Additionally, pins 1408 protrude from the pump 100 and register with the slots 1406. The pins 1408 must sufficiently protrude into, and optionally through, the slots 1406 to ensure sufficient interengagement between the adapter 1400 and the pump 100 to prevent dislodgement of the adapter 1400.

Figure 27:
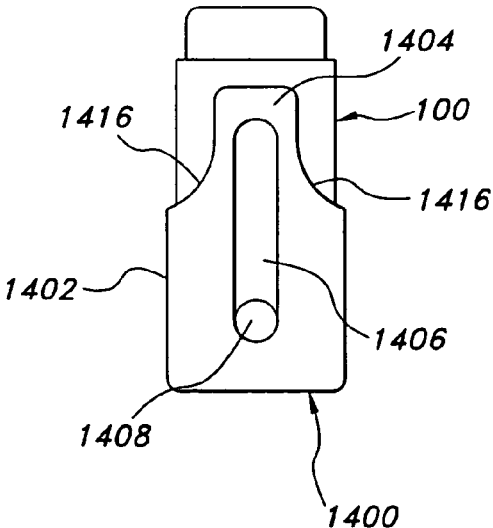

The interior of the body 1402 is dimensioned to allow for telescoping over the pump 100 with minimal clearance therebetween. In addition, a lip 1410 is preferably formed at the end of the body 1402 to act as a stable support for the pump 100, with the adapter 1400 being in a non-use position, as shown in FIG. 27.

With the structural arrangement described above, the adapter 1400 may be slid into an upward, non-use position, thereby advantageously covering the nozzle 160 and preventing contamination thereof. In addition, the lip 1410 provides a resting surface for the pump 100. The pins 1408 act as a stop against the slots 1406 and prevent excessive telescoping and thus allow for proper positioning of the adapter 1400 in the non-use position.

Figure 24:
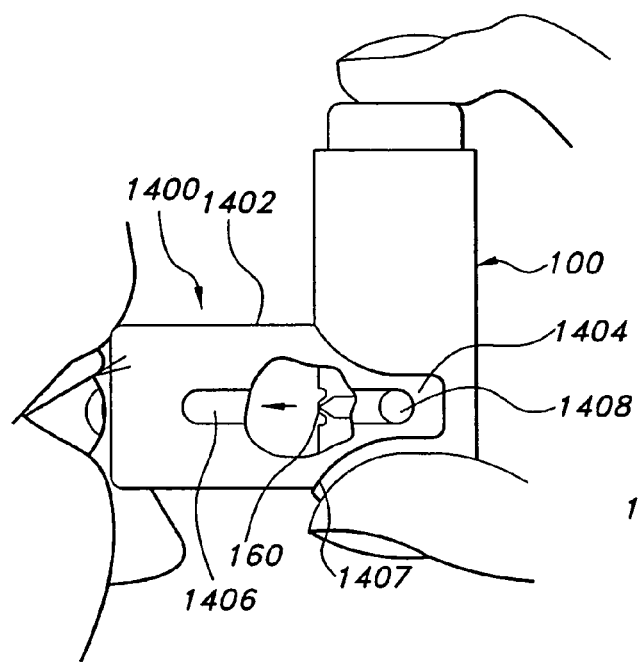
FIGS. 24–27 show an adapter utilizable with the subject invention.
Figure 25:
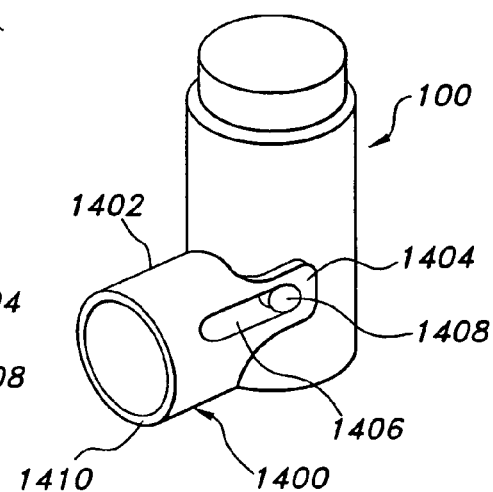
Figure 26:
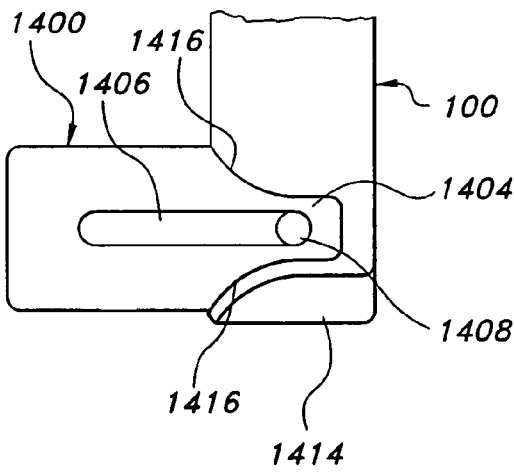

To use the pump 100, the adapter 1400 is slid downwardly, until the ends of the slots 1406 engage the pins 1408, and then pivoted about the pins 1408 into a use position, as shown in FIGS. 24–26. In the use position, the body 1412 is preferably formed to be generally concentric with the nozzle 106 to act as an alignment aid in dispensing fluid. As shown in FIG. 24, the adapter 1400 is particularly well-suited to act as an alignment aid in aligning a user's eye with the nozzle 106 is dispensing ophthalmic fluid. To provide further comfort to the user of the pump 100, a thumb depression 1414 may be formed in the base of the pump 100.

It is also preferred that curved surfaces 1416 be defined between the arms 1404, which match the contour of the pump 100, as shown in FIGS. 24–26. With matching surfaces, the adapter 1400 may be placed into a use position with stability relative to the pump 100 during dose administration.

As further variations of the adapter 1400, locking detents (such as detent 1407 shown in FIG. 24) may be provided to supply holding force for the adapter 1400 in the non-use and/or use positions. Furthermore, the slots 1406 need not be formed to extend completely through the adapter 1400, but rather may be formed "blind" with limited depth. Also, the adapter 1400 can be formed to telescope over the upper end of the pump if the nozzle is located there, such as with the pump 200 of the second embodiment of the subject invention.

As is readily apparent, numerous modifications and changes may readily occur to those skilled in the art, and hence it is not desired to limit the invention to the exact construction operation as shown and described, and accordingly, all suitable modification equivalents may be resorted to falling within the scope of the invention as claimed.

What is claimed is:

1. A pump for administering doses of fluid, said pump comprising:
   a reservoir formed to accommodate at least one of the doses of fluid;
   a fluid-collecting chamber in fluid communication with said reservoir, said fluid-collecting chamber including a dose-control portion which encompasses a volume defined by two dimensions;
   a piston disposed to reversibly slide within at least said dose-control portion so as to selectively displace at least a portion of fluid collected in said dose-control portion, wherein, with the pump being in a quiescent state, said piston is spaced from said dose-control portion;
   a nozzle, wherein said nozzle is located such that fluid displaced by said piston from said dose-control portion is generally urged towards said nozzle; and,
   at least one check valve disposed between said dose-control portion and said nozzle to selectively control flow,
   wherein said reservoir has a reduction in volume in response to reduction in fluid accommodated therein.

2. A pump as in claim 1, wherein fluid is pushed into at least said dose-control portion from said reservoir.

3. A pump as in claim 1, wherein fluid is drawn into at least said dose-control portion from said reservoir.

4. A pump as in claim 1, wherein a first of said dimensions is an axial length of said dose-control portion.

5. A pump as in claim 4, wherein a second of said dimensions is a diameter of said dose-control portion.

6. A pump as in claim 1, wherein said dose-control portion has a cylindrical shape.

7. A pump as in claim 1, wherein said check valve is spring-biased to close communication.

8. A pump as in claim 1, wherein said check valve is a spring-biased piston.

9. A pump as in claim 1, wherein said reservoir is not vented ambiently.

10. A pump as in claim 1, wherein a dose of fluid is approximately equal to or equal to said volume of said dose-control portion.

11. A pump as in claim 1, wherein said reservoir is non-vented.

* * * * *